US009765213B2

(12) United States Patent
Lewis et al.

(10) Patent No.: US 9,765,213 B2
(45) Date of Patent: Sep. 19, 2017

(54) DRUG CARRIERS COMPRISING AMPHILPHILIC BLOCK COPOLYMERS

(75) Inventors: Andrew Leonard Lewis, Surrey (GB); Steven Peter Armes, Sheffield (GB); Andrew W. Lloyd, Brighton (GB); Jonathan P. Salvage, Brighton (GB)

(73) Assignee: BIOCOMPATIBLES UK LIMITED, Surrey (GB)

( * ) Notice: Subject to any disclaimer, the term of this patent is extended or adjusted under 35 U.S.C. 154(b) by 0 days.

(21) Appl. No.: 13/355,910

(22) Filed: Jan. 23, 2012

(65) Prior Publication Data

US 2012/0157550 A1 Jun. 21, 2012

Related U.S. Application Data

(63) Continuation of application No. 10/506,805, filed as application No. PCT/GB03/00958 on Mar. 7, 2003, now abandoned.

(30) Foreign Application Priority Data

Mar. 7, 2002 (EP) ..................................... 02251505

(51) Int. Cl.
*A61K 47/30* (2006.01)
*A61P 35/00* (2006.01)
*C08L 53/00* (2006.01)
*A61K 9/107* (2006.01)
*C08F 293/00* (2006.01)

(52) U.S. Cl.
CPC ............ *C08L 53/00* (2013.01); *A61K 9/1075* (2013.01); *C08F 293/005* (2013.01)

(58) Field of Classification Search
CPC .... C08L 53/00; C08L 2666/02; C08L 9/1075; C08L 293/005
See application file for complete search history.

(56) References Cited

U.S. PATENT DOCUMENTS

| 5,846,558 | A | 12/1998 | Nielsen et al. |
| 6,852,816 | B2 | 2/2005 | Lewis et al. |
| 7,300,990 | B2 | 11/2007 | Lewis et al. |
| 2005/0123501 | A1 | 6/2005 | Lewis |
| 2005/0163743 | A1 | 7/2005 | Lewis |
| 2006/0069203 | A1 | 3/2006 | Lewis |
| 2006/0135714 | A1 | 6/2006 | Lewis |

FOREIGN PATENT DOCUMENTS

| WO | WO 99/43343 A1 | 9/1999 |
| WO | WO 02/28929 A1 | 4/2002 |

OTHER PUBLICATIONS

Butun et al., JACS, 1998, 120, 11818-11819.*
M. Wilhelm et al., "Poly(styrene-ethylene oxide) block copolymer micelle formation in water: A fluorescence probe study", Macromolecules, vol. 24, (1991), 1033-1040.
A. Lee et al., "Characterizing the Structure of pH Dependent Polyelectrolyte Block Copolymer Micelles", Macromolecules, vol. 32, (1999), pp. 4302-4310.
Coessens et al., "Functional polymers by atom transfer radical polymerization", Prog. Poly. Sci., 2001, vol. 26, 337-377.
Dalmark et al., "A Fikian Diffusion Transport Process with Features of Transport Catalysis", J. Gen. Physiol., Oct. 1981, vol. 78, 349-364.
E.J. Ashford et al., "First example of the atom transfer radical polymerisation of an acidic monomer: direct synthesis of methacrylic acid copolymers in aqueous media", Chem. Commun., (1999), pp. 1285-1286.
I. Astafieva et al., "Critical Micellization Phenomena in Block Polyelectrolyte Solutions", Macromolecules, vol. 26, (1993), pp. 7339-7352.
IPCS INCHEM, 1998, www.inchem.org/documents/icsc/icsc/eics1113.htm.
Ishihara, et al., Polymeric Lipid Nanosphere Consisting of Water-Soluble Poly(2-methacryloyloxyethyl phosphorylcholine-co-n-butyl methacrylate), Polymer Journal, 1999, pp. 1231-1236, vol. 31, No. 12.
ISO, Biological evaluation of medical device.
Kataoka et al., "Block copolymer micelles for drug delivery: design, characterization and biological significance", Advanced Drug Delivery Reviews, 2001, vol. 47(1), 113-131.
Konno et al., 2001, Biomaterials, 22, 1883-1889.
Lobb et al., Facile Synthesis of Well-Defined, Biocompatible Phosphorylcholine-Based Methacrylate Copolymers via Atom Transfer Radical Polymerication at 20 degreesC, J. Am. Chem. Soc., 2001, vol. 123, 7913-7914.
M. Jones et al., "Polymeric micelles—a new generation of colloidal drug carriers", European Journal of Pharmaceutics and Biopharmaceutics, vol. 48, (1999), pp. 101-111.
Novel biocompatible phosphorylcholine-based self-assembled nanoparticles for drug delivery.
T. Inoue et al., "An AB block copolymer of oligo(methacrylate) and poly(acrylic acid) for micellar delivery of hydrophobic drugs", Journal of Controlled Release, vol. 51, (1998), pp. 221-229.

(Continued)

*Primary Examiner* — Kyle Purdy
(74) *Attorney, Agent, or Firm* — Sughrue Mion, PLLC

(57) ABSTRACT

An aqueous composition comprises an amphiphilic block copolymer, having a hydrophilic block comprising pendant zwitterionic groups and a hydrophobic block, and a biologically active compound associated with the polymer. The polymer is preferably in the form of micelles, and preferably the biological active is a hydrophobic drug. The hydrophilic block is preferably formed from acrylic monomer including phosphorylcholine groups. The hydrophobic group is suitably formed from monomer which has groups which can be ionised at useful pH's, especially tertiary amine groups. Micelles may be formed by dissolving the block copolymer in aqueous solvent at a pH at which the amine groups are protonated then raising the pH to a value at which the amine groups are substantially deprotonated, whereupon micelles spontaneously form. The preformed micelles are then contacted with active, under conditions such that solubilisation of the active occurs. The active may be for tumour treatment.

30 Claims, 18 Drawing Sheets

(56) References Cited

OTHER PUBLICATIONS

T. Konno, et al., "Enhanced solubility of paclitaxel using water-soluble and biocompatible 2-methacryloyloxyethyl phosphorylcholine polymers," Journal of Biomedical Materials Research Part A, vol. 65A, Issue 2, May 1, 2003, pp. 210-215.
Ueda, et al., Preparation of 2-Methacryloyloxyethyl Phosphorylcholine Copolymers with Alkyl Methacrylates and Their Blood Compatibility, Polymer Journal, 1992, pp. 1259-1269, vol. 24, No. 11.
V. Alakhov et al., "Block copolymer-based formulation of doxorubicin. From cell screen to clinical trials", Colloids & Surfaces B: Biointerfaces, vol. 16 (1-4), (1999), pp. 113-134.
V. Alakhov et al., "Block Copolymer-Based Formulations of Doxorubicin Effective Against Drug Resistant Tumors", Biomedical Polymers and Polymer Therapeutics, (2001), pp. 121-137.
V. Bütün et al., "Synthesis and aqueous solution properties of near-monodisperse tertiary amine methacrylate homopolymers and diblock copolymers", Polymer, vol. 42, (2001), pp. 593-6008.

\* cited by examiner

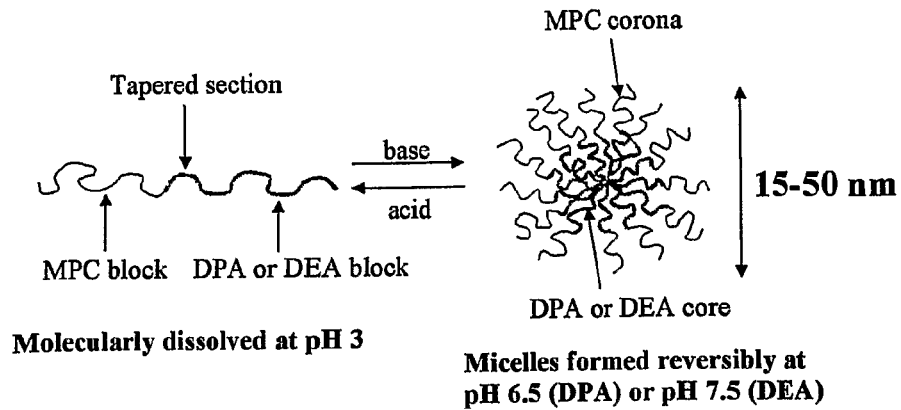
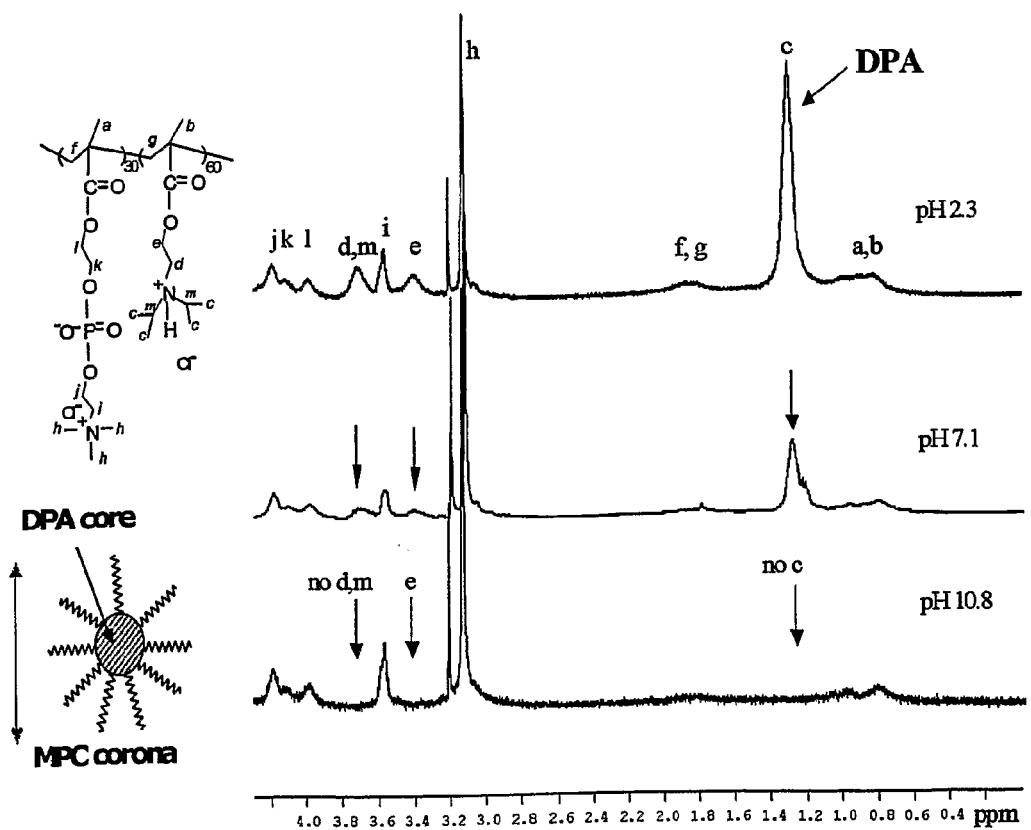
Figure 3
Figure 4

DRUG CARRIERS COMPRISING AMPHILPHILIC BLOCK COPOLYMERS

CROSS REFERENCE TO RELATED APPLICATIONS

This application is a continuation of pending U.S. application Ser. No. 10/506,805, filed Jan. 19, 2005, which is a national stage entry of PCT/GB03/00958, filed Mar. 7, 2003, which claims priority from European Patent Application No. 02251505.0, filed Mar. 7, 2002, the contents of all of which are incorporated herein by reference in their entirety.

BACKGROUND OF THE INVENTION

The present invention relates to block copolymers for micellar delivery of drugs. It is of particular value for delivery of hydrophobic drugs.

Micelle based drug delivery systems have been developed which are based on amphiphilic copolymers. Such copolymers should have a hydrophobic moiety and a hydrophilic moiety. In a micelle, the hydrophobic moieties aggregate to form a core, with the hydrophilic moieties being revealed at the surface of the micelle where they associate with water. The micelles can solubilise poorly water-soluble drugs in their inner core. Their small size renders them suitable for systemic delivery of drugs. The core-shell structure provides some protection for the drug in the core during transport to a target cell.

Although random copolymers may be used, in which some of the monomers have hydrophobic pendant groups, most work has focussed on block copolymers. AB diblock copolymers and ABA triblock copolymers, A being the hydrophilic block and B being the hydrophobic block have been investigated. In most of the block copolymers tested to date, the hydrophilic blocks have been provided by polyethylene oxide moieties. The hydrophobic block may be a polypropylene oxide block, a hydrophobic polypeptide (such as poly($\beta$-benzyl-L-aspartate)), a polyester (poly(DL-lactic acid)) or poly($\epsilon$-caprolactone). Polystyrene and poly(methylmethacrylate) have also been investigated as constituents of the core.

Alakhov et al in Biomedical Polymers and Polymer Therapeutics, 2001, eds Chiellini et al Kluwer Academic/Plenum publishers, New York, 121 to 137, describe the use of polyethylene oxide-polypropylene oxide block copolymers to deliver doxorubicin. Such compounds are commercially available with low poly-dispersity (of molecular weight) under the trade name Pluronic and Poloxamer (trade marks). They investigate the effect of the average molecular weight and the hydrophilic/lipophilic balance (HLB) of the block copolymer upon cytotoxicity against a panel of cell lines.

Jones et al in Eur. J. Pharm. Biopharm. 48 (1999) 101 to 111 review the disclosures of various block copolymers as colloidal drug carriers, and explains various ways in which micelles are formed with hydrophobic drug in the core.

Inoue et al in J. Cont. Rel. 51(1998) 221 to 229 describe an AB block copolymer having amphiphilic properties, in which one block is formed of methyl methacrylate (the hydrophobic core) and the other block is formed of acrylic acid units. Polymerisation is conducted by initially forming an oligomer of methylmethacrylate units, and using this as the initiator for polymerising a block of acrylic acid. The average molecular weight of the hydrophobic block was said to be 4300, although the molecular weight of the block copolymer was not stated. The physical form of the drug delivery system appeared to involve non-micellar structures, termed "unimers".

In our earlier applications No WO-A-0228929, not published at the priority date hereof we described the polymerisation of zwitterionic monomers by atom transfer radical polymerisation techniques, some of the polymers were block copolymers. A general suggestion was made that the polymers may have utility in delivery of drugs.

BRIEF SUMMARY OF THE INVENTION

According to the present invention there is provided an aqueous composition comprising an amphiphilic block copolymer having a hydrophilic block and a hydrophobic block, dispersed in the solution, and a biologically active compound associated with the polymer, characterised in that the hydrophilic block has pendant zwitterionic groups.

The term "associated with" in the present invention means that the biologically active molecule has some association with the polymer such that its solubility, bioavailability, immunogenicity, or toxicity, is affected by the interaction with the polymer. Although the association is normally by way of the presence of micelles in which a biologically active compound is present in the core, it may involve other types of interaction, for instance the "unimer" type solutes described by Inoue et al (op. cit). It may involve covalent conjugation, but generally involves non-covalent interactions, such as electro-static, or preferably hydrophobic interactions.

BRIEF DESCRIPTION OF THE DRAWINGS

The following figures illustrate the invention:
FIG. 3 illustrates the effect of pH on the solubilisation of a hydrophobic drug for block copolymers used in the invention;
FIG. 4 shows the results of Example 4.

DETAILED DESCRIPTION OF THE INVENTION

Figure 1:
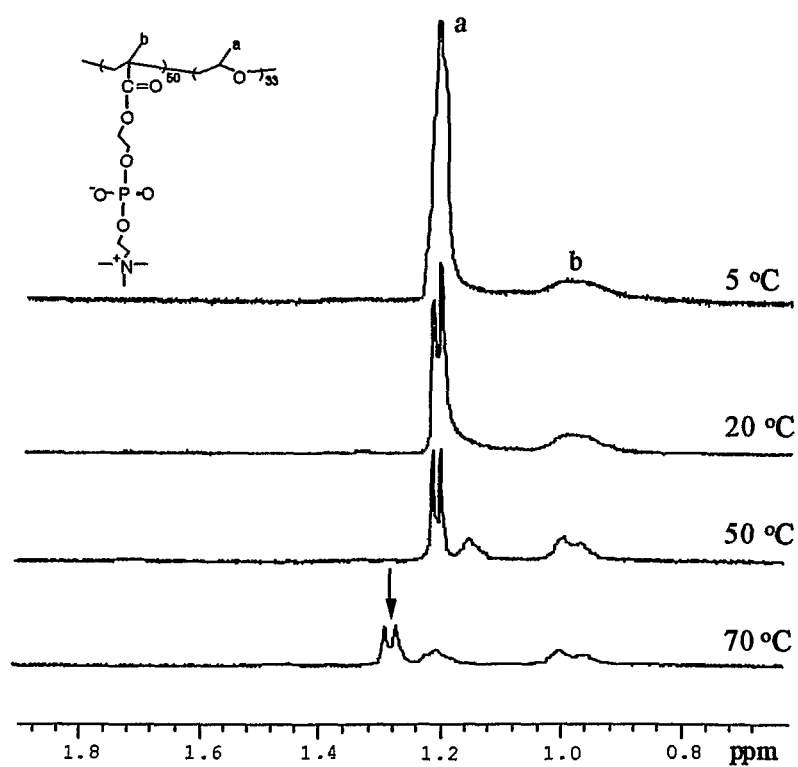
FIGS. 1 and 2 indicate the results of example 3.

Although the active may be a water-soluble drug, preferably it is relatively water-insoluble, generally soluble in an organic solvent. Generally the active has a solubility such that it has a partition coefficient (log P) between octanol and water of at least 1.0, preferably at least 1.5, more preferably at least 2.0. The active will, in the presence of micelles of the amphiphilic block copolymer used in the invention, be preferentially partitioned into the hydrophobic core of micelles, or otherwise associated with the hydrophobic block. Examples of suitable drugs are given below.

Although the hydrophilic block may be based on condensation polymers, such as polyesters, polyamides, polyanhydrides, polyurethanes, polyethers, polyimines, polypeptides, polyureas, polyacetals, polysaccharides or polysiloxanes, preferably the hydrophilic block is based on a radical polymerised addition polymer of ethylenically unsaturated monomers. Generally the monomers from which the block is formed themselves have zwitterionic pendant groups which remain unchanged in the polymerisation process. It may alternatively be possible to derivatise a functional pendant group of a monomer to render it zwitterionic after polymerisation.

Suitable ethylenically unsaturated zwitterionic monomers have the general formula $$YBX \qquad\qquad I$$

in which Y is an ethylenically unsaturated group selected from $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

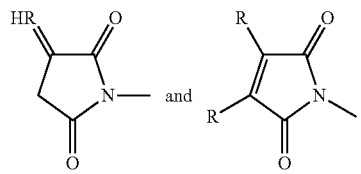

A is $-O-$ or $NR^1$;
$A^1$ is selected from a bond, $(CH_2)_lA^2$ and $(CH_2)_lSO_3-$ in which 1 is 1 to 12;
$A^2$ is selected from a bond, $-O-$, $O-CO-$, $CO-O$, $CO-NR^1-$, $-NR^1-CO$, $O-CO-NR^1-$, $NR^1-CO-O-$;
R is hydrogen or $C_{1-4}$ alkyl;
$R^1$ is hydrogen, $C_{1-4}$-alkyl or BX;
$R^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

Preferably X is an ammonium, phosphonium, or sulphonium phosphate or phosphonate ester zwitterionic group, more preferably a group of the general formula II

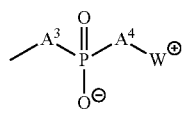

in which the moieties $A^3$ and $A^4$, which are the same or different, are $-O-$, $-S-$, $-NH-$ or a valence bond, preferably $-O-$, and $W^+$ is a group comprising an ammonium, phosphonium or sulphonium cationic group and a group linking the anionic and cationic moieties which is preferably a $C_{1-12}$-alkanediyl group,
preferably in which $W^+$ is a group of formula

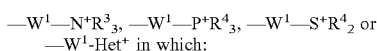

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Monomers in which X is of the general formula in which $W^+$ is $W^1N^{\oplus}R^3_3$ may be made as described in our earlier specification WO-A-9301221. Phosphonium and sulphonium analogues are described in WO-A-9520407 and WO-A-9416749.

Generally a group of the formula II has the preferred general formula III

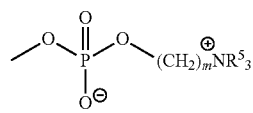

where the groups $R^5$ are the same or different and each is hydrogen or $C_{1-4}$ alkyl, and m is from 1 to 4, in which preferably the groups $R^5$ are the same preferably methyl.

In phosphobetaine based groups, X may have the general formula IV

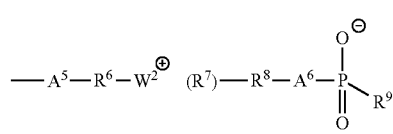

in which $A^5$ is a valence bond, $-O-$, $-S-$ or $-NH-$, preferably $-O-$;

$R^6$ is a valence bond (together with $A^5$) or alkanediyl, $-C(O)$alkylene- or $-C(O)NH$ alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;
$R^6$ is a $C_{2-6}$ alkanediyl;
$W^2$ is $NR^7$:
each $R^7$ is $C_{1-4}$ alkyl;
$R^8$ is $C_{2-6}$ alkanediyl;
$A^6$ is O; and
$R^9$ is $C_{1-4}$ alkoxy.

Alternatively X may be a zwitterion in which the anion comprises a sulphate, sulphonate or carboxylate group.

One example of such a group is a sulphobetaine group, of the general formula V

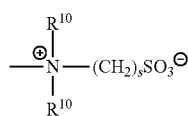

V where the groups $R^{10}$ are the same or different and each is hydrogen or $C_{1-4}$ alkyl and s is from 2 to 4.

Preferably the groups $R^{10}$ are the same. It is also preferable that at least one of the groups $R^{10}$ is methyl, and more preferable that the groups $R^{36}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI

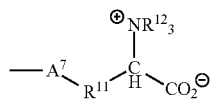

VI in which $A^7$ is a valence bond, —O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^{\oplus}(O)R^{13})_2(CH_2)_rCOO$— in which the $R^{13}$ groups are the same or different and each is hydrogen or $R_{1-4}$ alkyl and r is 2 to 6, preferably 2 or 3.

In the zwitterionic monomer of the general formula I it is preferred that the ethylenic unsaturated group Y is $H_2C=CR-CO-A-$. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-2'-trimethylammonium ethyl phosphate inner salt (MPC). Mixtures of zwitterionic monomers each having the above general formula may be used.

The hydrophobic block may be formed of condensation polymers, such as polyethers, polyesters, polyamides, polyanhydrides polyurethanes, polyimines, polypeptides, polyureas, polyacetals, polysaccharides or polysiloxanes. One example of a suitable hydrophobic block is polyalkylene oxide, usually polypropylene oxide, that is the same type of block as has been used in the well-studied Pluronic/Poloxamer based systems. Another is polyethylenimine, copolymers of which with polyalkylene oxides have been investigated as drug delivery components. One type of highly hydrophobic block is poly(dimethylsiloxane). In one preferred embodiment the type of polymer forming the hydrophobic block is the same as that forming the hydrophilic block. Preferably the polymer is formed by radical polymerisation of ethylenically unsaturated monomers.

The hydrophobic block may be nonionic and substantially non-ionisable under pH conditions in the range 4 to 10. Preferably, however, the hydrophobic block comprises pendant groups which are ionisable, having a $pK_A$ or $pK_B$ in the range 4 to 10, preferably in the range 5 to 9, for instance in the range 6 to 8. In the specification, the $pK_A$ or $pK_B$, as the case may be, of a group in a polymer is determined on the basis of a polymer system (and not assumed to be the same as the $pK_A$'s or $pK_B$'s of similar moieties in non-polymeric systems).

It is preferred that the hydrophobic block comprise pendant cationisable moieties preferably as pendant groups. Cationisable moieties are, for instance, primary, secondary or tertiary amines, capable of being protonated at pH's in the range 4 to 10. Alternatively the group may be a phosphine.

Suitable monomers from which the hydrophobic block may be formed have the general formula VII $Y^1B^1Q$          VII in which $Y^1$ is selected from $H_2C=CR^{14}-CO-A^8-$, $H_2C=CR^{14}-C_6H_4-A^9-$, $H_2C=CR^{14}-CH_2A^{10}$, $R^{16}O-CO-CR^{14}=CR^{14}-CO-O$, $R^{14}CH=CH-CO-O-$, $R^{14}CH=C(COOR^{16})CH_2-CO-O-$,

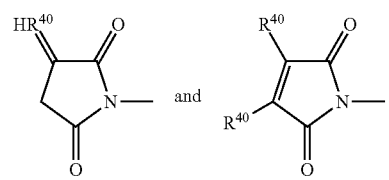

and $A^8$ is —O— or $NR^{15}$;
$A^9$ is selected from a bond, $(CH_2)_qA^{10}$ and $(CH_2)_qSO_3$— in which q is 1 to 12;
$A^{10}$ is selected from a bond, —O—, O—CO—, CO—O—, CO—$NR^{15}$—,
—$NR^{15}$—CO—, O—CO—$NR^{15}$—, $NR^{15}$—CO—O—;
$R^{14}$ is hydrogen or $C_{1-4}$ alkyl;
$R^{15}$ is hydrogen, $C_{1-4}$-alkyl or $B^1Q$;
$R^{16}$ is hydrogen or $C_{1-4}$ alkyl;

$B^1$ is a bond, or a straight branched alkanediyl, alkylene oxaalkylene, or alkylene (oligooxalkylene) group, optionally containing one or more fluorine substituents; and Q is a cationic or cationisable group of the formula $-NR^{17}_p$, $-PR^{17}_p$ and $SR^{17}_r$, in which p is 2 or 3, r is 1 or 2, the groups $R^{43}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{43}$ groups may be substituted by amino or hydroxyl groups or halogen atoms.

Preferably $Y^1$ is $H_2C=CR^{14}-CO-A^8-$ where $R^{14}$ is H or methyl and $A^8$ is O or NH.

Preferred groups $B^1$ are alkanediyl, usually with linear alkyl chains and preferably having 2 to 12 carbon atoms, such as 2 or 3 carbon atoms.

Preferably Q is $NR^{17}_2$ where $R^{17}$ is $C_{1-12}$-alkyl. Preferably both $R^{17}$'s are the same. Particularly useful results have been achieved where the groups $R^{17}$ are $C_{1-4}$ alkyl, especially ethyl, methyl or isopropyl.

Either or both the hydrophobic and hydrophilic blocks may include comonomers, for instance to provide functionality, control over hydrophobicity, control over pH sensitivity, $pK_A$ or $pK_B$ as the case may be, control over temperature sensitivity or as general diluents. For instance comonomers providing functionality may be useful to provide conjugation of pendant groups following polymerisation and/or micelle formation, to targeting moieties, or to provide for conjugation between the biologically active molecule and the polymer. Alternatively, functional groups may allow for crosslinking of the polymer following micelle formation, to confer increased stability on the micellar structure.

Examples of suitable comonomers are compounds of the general formula VIII

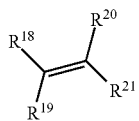

VIII in which $R^{18}$ is selected from hydrogen, halogen, $C_{1-4}$ alkyl and groups $COOR^{22}$ in which $R^{22}$ is hydrogen and $C_{1-4}$ alkyl;

$R^{19}$ is selected from hydrogen, halogen and $C_{1-4}$ alkyl;

$R^{20}$ is selected from hydrogen, halogen, $C_{1-4}$ alkyl and groups $COOR^{22}$ provided that $R^{18}$ and $R^{20}$ are not both $COOR^{22}$; and $R^{21}$ is a $C_{1-10}$ alkyl, a $C_{1-20}$ alkoxycarbonyl, a mono- or di-($C_{1-20}$ alkyl)amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and trialkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups;

or $R^{21}$ and $R^{20}$ or $R^{21}$ and $R^{19}$ may together form $-CONR^{23}CO-$ in which $R^{23}$ is a $C_{1-20}$ alkyl group.

It is preferred for at least two of the groups $R^{18}$, $R^{19}$, $R^{20}$ and $R^{21}$ to be halogen or, more preferably, hydrogen atoms. Preferably $R^{18}$ and $R^{19}$ are both hydrogen atoms. It is particularly preferred that compound of general formula X be a styrene-based or acrylic based compound. In styrene based compounds $R^{21}$ represents an aryl group, especially a substituted aryl group in which the substituent is an amino alkyl group, a carboxylate or a sulphonate group. Where the comonomer is an acrylic type compound, $R^{21}$ is an alkoxycarbonyl, an alkyl amino carbonyl, or an aryloxy carbonyl group. Most preferably in such compounds $R^{21}$ is a $C_{1-20}$-alkoxy carbonyl group, optionally having a hydroxy substituent. Acrylic compounds are generally methacrylic in which case $R^{20}$ is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo $(C_{2-3}$ alkoxy) $C_{2-18}$-alkyl (alk)-acrylate, or -acrylamide, styrene, vinylacetate or N-vinyllactam.

The block copolymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on drug-containing micelles. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed by instance by the random copolymerisation of monounsaturated macromers and monomers.

For optimum micelle formation, the block copolymers should have controlled molecular weights. It is preferable for each of the blocks to have molecular weight controlled within a narrow band, that is to have a narrow polydispersity. The polydispersity of molecular weight should, for instance, be less than 2.0, more preferably less than 1.5, for instance in the range 1.1 to 1.4.

The degree of polymerisation of the hydrophobic block is in the range 5 to 2000, preferably 10 to 500, more preferably 10 to 250. The hydrophilic block has a degree of polymerisation in the range 2 to 1000, preferably 5 to 250 more preferably 10 to 100. Generally the relative lengths of the hydrophobic to hydrophilic blocks is in the range 1:5 to 10:1, preferably 1:1 to 5:1.

It may be possible to synthesise the block copolymer by initial formation of a low polydispersity, low molecular weight initial block using control of initiator and chain transfer agent (which permanently terminates chain formation), with the initial block then being derivatised to act as a suitable radical initiator in a subsequent block forming step, by the technique described by Inoue et al op. cit. Low polydispersity low molecular weight polymers which may be derivatised to form a substrate for the block polymerisation of second block are commercially available. Such polymers are, for instance, poly(alkylene oxides), poly(dimethyl siloxanes), polyimides, acrylic copolymers, etc. Some examples in which oligomers are derivatised to form initiator compounds for controlled radical polymerisation are described below. Preferably, the polymerisation of at least one of the blocks and preferably both the blocks is by controlled radical polymerisation for instance a living radical polymerisation process.

A living radical polymerisation process may be a group transfer radical polymerisation, for instance in which an N→O, or other carbon-, sulphur-, and oxygen-centered radical group is transferred from an initiator compound to a monomer. Preferably, however, the process is an atom transfer radical polymerisation process. Preferably such a process is used to form each block of the block copolymer.

In the atom or group transfer radical polymerisation process, the initiator has a radically transferable atom or group, and the catalyst comprises a transition metal compound and a ligand, in which the transition metal compound is capable of participating in a redox cycle with the initiator and dormant polymer chain, and the ligand is either any N—, O—, P—or S—containing compound which can coordinate with the transition metal atom in a σ-bond, or any carbon-containing compound which can coordinate with the transition metal in a π-bond, such that direct bonds between the transition metal and growing polymer radicals and not formed.

Preferably the radical initiator is of the general formula IX

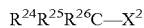

where:

$X^2$ is selected from the group consisting of Cl, Br, I, $OR^{27}$, $SR^{28}$, $SeR^{28}$, $OP(=O)R^{28}$, $OP(=O)(OR^{28})_2$, $O-N(R^{28})_2$ and $S-C(=S)N(R^{28})_2$, where $R^7$ is alkyl of from 1 to 20 carbon atoms in which each of the hydrogen atoms may be independently replaced by halide, $R^{28}$ is aryl or a straight or branched $C_1$-$C_{20}$ alkyl group, and where an $N(R^{28})_2$ group is present, the two $R^{28}$ groups may be joined to form a 5- or 6-membered heterocyclic ring; and $R^{24}$, $R^{25}$ and $R^{26}$ are each independently selected from the group consisting of H, halogen, $C_1$-$C_{20}$ alkyl, $C_3$-$C_8$ cycloalkyl, $C(=O)R^{29}$, $C(=O)NR^{30}R^{31}$, COCl, OH, CN, $C_2$-$C_{20}$ alkenyl, $C_2$-$C_{20}$ alkenyl oxiranyl, glycidyl, aryl, heterocyclyl, aralkyl, aralkenyl, $C_1$-$C_6$ alkyl in which from 1 to all of the hydrogen atoms are replaced with halogen, $C_1$-$C_6$ alkyl substituted with from 1 to 3 substituents selected from the group consisting of $C_1$-$C_4$ alkoxy, aryl, heterocyclyl, $C(=O)R^{29}$, $C(=O)NR^{30}R^{31}$, $-CR^{25}R^{26}X^2$, oxiranyl and glycidyl;

where $R^{29}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups; and $R^{30}$ and $R^{31}$ are independently H or alkyl of from 1 to 20 carbon atoms which alkyl groups, in turn may have substituents selected from acyl, alkoxycarbonyl, alkenoxycarbonyl, aryl and hydroxy, or $R^{30}$ and $R^{31}$ may be joined together to form an alkanediyl group of from 2 to 5 carbon atoms, thus forming a 3- to 6-membered ring;

such that not more than two of $R^{24}$, $R^{25}$ and $R^{26}$ are H.

In the initiator of the general formula IX it is preferred that no more than one of $R^{24}$, $R^{25}$ and $R^{26}$, and preferably none, is hydrogen. Suitably at least one, and preferably both of $R^{24}$ and $R^{25}$ is methyl. $R^{26}$ is suitably a group $CO-R^{29}$ in which $R^{29}$ is preferably alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups.

Since any of $R^{24}$, $R^{25}$ and $R^{26}$ may comprise a substituent $C^{25}R^{26}X^2$, the initiator may be di-, oligo- or poly-functional, which may be of use to form A-B-A type copolymers or star polymers.

Selection of a suitable initiator is based on various considerations. Where the polymerisation is carried out in the liquid phase, in which the monomers are dissolved, it is preferable for the initiator to be soluble in that liquid phase. The initiator is thus selected for its solubility characteristics according to the solvent system which in turn is selected according to the monomers being polymerised.

Water-soluble initiators include, for instance the reaction product of monomethoxy-capped oligo(ethylene oxide) with 2-bromoisobutyryl bromide (OEGBr), 4-bromo-α-toluic acid or ethyl 2-bromopropanoic acid or 2-(N,N-dimethylamino) ethyl-2'-bromoisobutyrate.

The portion of the initiator $-C-R^{24}R^{25}R^{26}$ becomes joined to the first monomer of the growing polymer chain. The group $X^2$ becomes joined to the terminal unit of the polymer chain. Selection of a suitable initiator is determined in part by whether a terminal group having particular characteristics is required for subsequent functionality. Subsequent reactions of the product polymer are described below. The residue of the initiator at one or other end of the polymer may be reacted with biologically active moieties, such as targetting groups. Alternatively the initiator itself may comprise a group conferring useful targetting or other biological activity in the product polymer. Alternatively the initiator may comprise a highly hydrophobic group, which is polymeric and which may consequently form the part of the hydrophobic block. Suitable hydrophobic polymers which may be converted into initiators are, for instance, polypropylene oxide) and poly(dimethyl siloxane).

In an atom or group radical transfer polymerisation process the transition metal compound which comprises a component of the catalyst is $M_t^{n+}X^3_n$, where:

$M_t^{n+}$ may be selected from the group consisting of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W^{3+}$, $Mn^{2+}$, $Mn^{3+}$, $Mn^{4+}$, $Rh^{3+}$, $Rh^{4+}$, $Re^{2+}$, $Re^{3+}$, $Co^+$, $Co^{2+}$, $Co^{3+}$, $V^{2+}$, $V^{3+}$, $Zn^+$, $Zn^{2+}$, $Ni^{2+}$, $Ni^{3+}$, $Au^+$, $Au^{2+}$, $Ag^+$ and $Ag^{2+}$;

$X^3$ is selected from the group consisting of halogen, $C_1$-$C_6$-alkoxy, $(SO_4)_{1/2}$, $(PO_4)_{1/3}$, $(R^{32}PO_4)_{1/2}$, $(R^{32}_2PO_4)$, triflate, hexafluorophosphate, methanesulphonate, arylsulphonate, CN and $R^{33}CO_2$, where $R^{32}$ is aryl or a straight or branched $C_{1-20}$ alkyl and $R^{33}$ is H or a straight or branched $C_1$-$C_6$ alkyl group which may be substituted from 1 to 5 times with a halogen; and n is the formal charge on the metal (0≤n≤7).

Preferably $X^3$ is halide, most preferably chloride or bromide. Particularly suitable transition metal compounds are based on copper or ruthenium, for instance CuCl, CuBr or $RuCl_2$.

In the catalyst, the ligand is preferably selected from the group consisting of:

a) compounds of the formulas:

$$R^{34}-Z-R^{35}$$

and $$R^{34}-Z-(R^{36}-Z)_m-R^{35}$$

where:

$R^{34}$ and $R^{35}$ are independently selected from the group consisting of H, $C_1$-$C_{20}$ alkyl, aryl, heterocyclyl and $C_1$-$C_6$ alkoxy, $C_1$-$C_4$ dialkylamino, $C(=O)R^{37}$ and $A^7C(=O)R^{40}$, where $A^7$ may be $NR^{41}$ or O; $R^{37}$ is alkyl of from 1 to 20 carbon atoms, aryloxy or heterocyclyloxy; $R^{40}$ is H, straight or branched $C_1$-$C_{20}$ alkyl or aryl and $R^{41}$ is hydrogen, straight or branched; $C_{1-20}$-alkyl or aryl; or $R^{34}$ and $R^{35}$ may be joined to form, together with Z, a saturated or unsaturated ring;

Z is O, S, $NR^{42}$ or $PR^{42}$, where $R^{42}$ is selected from the same group as $R^{34}$ and $R^{35}$, and where Z is $PR^{42}$, $R^{42}$ can also $C_1$-$C_{20}$ alkoxy or Z may be a bond, $CH_2$ or a fused ring, where one or both of $R^{34}$ and $R^{35}$ is heterocyclyl, each $R^{36}$ is independently a divalent group selected from the group consisting of $C_1$-$C_8$ cycloalkanediyl, $C_1$-$C_8$ cycloalkenediyl, arenediyl and heterocyclylene where the covalent bonds to each Z are at vicinal positions or $R^{36}$ may be joined to one or both of $R^{34}$ and $R^{35}$ to formulate a heterocyclic ring system; and m is from 1 to 6;

b) CO;

c) porphyrins and porphycenes, which may be substituted with from 1 to 6 halogen atoms, $C_{1-6}$ alkyl groups, $C_{1-6}$-alkoxy groups, $C_{1-6}$ alkoxycarbonyl, aryl groups, heterocyclyl groups, and $C_{1-6}$ alkyl groups further substituted with from 1 to 3 halogens;

d) compounds of the formula $R^{43}R^{44}C(C(=O)R^{45})_2$, where $R^{45}$ is $C_{1-20}$ alkyl, $C_{1-20}$ alkoxy, aryloxy or heterocyclyloxy; and each of $R^{43}$ and $R^{44}$ is independently selected from the group consisting of H, halogen, $C_{1-20}$ alkyl, aryl and heterocyclyl, and $R^{43}$ and $R^{44}$ may be joined to form a $C_{1-8}$ cycloalkyl ring or a hydrogenated aromatic or heterocyclic ring, of which the ring atoms may be further substituted with 1 to 5 $C_{1-6}$ alkyl groups, $C_{1-6}$ alkoxy groups, halogen atoms, aryl groups, or combinations thereof; and e) arenes and cyclopentadienyl ligands, where said cyclopentadienyl ligand may be substituted with from one to five methyl groups, or may be linked through and ethylene or propylene chain to a second cyclopentadienyl ligand.

Selection of a suitable ligand is, for instance, based upon the solubility characteristics and/or the separability of the catalyst from the product polymer mixture. Generally it is desired for the catalyst to be soluble in a liquid reaction mixture, although under some circumstances it may be possible to immobilise the catalyst, for instance an a porous substrate. For the preferred process, which is carried out in the liquid phase, the ligand is soluble in a liquid phase. The ligand is generally a nitrogen containing ligand. The preferred ligand may be a compound including a pyridyl group, such as bipyridine, or a compound including a pyridyl group and an imino moiety, such as

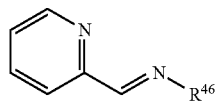

where $R^{46}$ is a suitable alkyl group, the substituent being variable and adaptable to confer desired solubility characteristics, triphenylphosphine or 1,1,4,7,10,10-hexamethyl-triethylene tetramine.

Such ligands are usefully used in combination with copper chloride, copper bromide and ruthenium chloride transition metal compounds as part of the catalyst.

A living radical polymerisation process is preferably carried out to achieve a degree of polymerisation in the or each block in the range 2 to 2000. Preferably the degree of polymerisation is in the range 5 to 1000, more preferably in the range 10 to 100. In the preferred group or atom transfer radical polymerisation technique, the degree of polymerisation is directly related to the initial ratios of initiator to monomer. Preferably the ratio is in the range 1:(2 to 2000), more preferably in the range of 1:(5 to 1000), most preferably in the range 1:(10 to 100).

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8:1.25). Preferably the range is about 1:1.

In the living radical polymerisation process, the catalyst may be used in amounts such that a molar equivalent quantity as compared to the level of initiator is present. However, since catalyst is not consumed in the reaction, it is generally not essential to include levels of catalyst as high as of initiator. The ratio of catalyst (based on transition metal compound) to initiator is preferably in the range 1:(1 to 50), more preferably in the range 1:(1 to 10).

Whilst the polymerisation reaction may be carried out in the gaseous phase, it is more preferably carried out in the liquid phase. The reaction may be heterogeneous, that is comprising a solid and a liquid phase, but is more preferably homogeneous. Preferably the polymerisation is carried out in a single liquid phase. Where the monomer is liquid, it is sometimes unnecessary to include a non-polymerisable solvent. More often, however, the polymerisation takes place in the presence of a non-polymerisable solvent. The solvent should be selected having regard to the nature of the zwitterionic monomer and any comonomer, for instance for its suitability for providing a common solution containing both monomers. The solvent may comprise a single compound or a mixture of compounds.

It has been found that, especially where the zwitterionic monomer is MPC, that it is may be desirable to include water in the polymerisation mixture. In such processes water should be present in an amount in the range 10 to 100% by weight based on the weight of ethylenically unsaturated monomer. Preferably the total non-polymerisable solvent comprised 1 to 500% by weight based on the weight of ethylenically unsaturated monomer. It has been found that the zwitterionic monomer and water should be in contact with each other for as short a period as possible prior to contact with the initiator and catalyst. It may be desirable therefore for all the components of the polymerisation other than the zwitterionic monomer to be premixed and for the zwitterionic monomer to be added to the premix as the last additive.

It is often desired to copolymerise MPC or other zwitterionic monomer with a comonomer which is insoluble in water. In such circumstances, a solvent or co-solvent (in conjunction with water) is included to confer solubility on both MPC and the more hydrophobic monomer. Suitable organic solvents are ethers, esters and, most preferably, alcohols. Especially where a mixture of organic solvent and water is to used, suitable alcohols are $C_{1-4}$-alkanols. Methanol is found to be particularly suitable in the polymerisation process of the invention.

The process may be carried out at raised temperature, for instance up to 60 to 80° C. However it has been found that the process proceeds sufficiently fast at ambient temperature.

The living radical polymerisation process has been found to provide polymers of zwitterionic monomers having a polydispersity (of molecular weight) of less than 1.5, as judged by gel permeation chromatography. Polydispersities in the range 1.2 to 1.4 for the or each block are preferred.

According to a further aspect of the invention there is provided a new method of forming an aqueous composition comprising an amphiphilic block copolymer and a biologically active compound, in which the copolymer comprises a hydrophilic block and a hydrophobic block, an aqueous dispersion of empty copolymer micelles is formed and the micellar dispersion is contacted with biologically active compound under conditions such that the biologically active compound becomes associated with the copolymer in the micelles, characterised in that the hydrophilic block has pendant zwitterionic groups.

Where the composition of the invention comprises micelles of block copolymer with biologically active molecule in the core, this may be formed by a variety of techniques. The process may involve simple equilibration of the drug and polymer micelles in water, at a concentration above the critical micelle concentration (CMC) of the block copolymer. For instance drug may be contacted in solid form with an aqueous dispersion of polymer micelles and incubated, optionally with shaking, to solubilise the active in the dispersed micelles. Alternatively, drug dissolved in organic solvent may be emulsified into an aqueous dispersion of polymer micelles, whereby solvent and biologically active compound become incorporated into the core of the micelles, followed by evaporation of solvent from the system.

An advantage of the present invention where the hydrophobic block is pH sensitive, is that micelles may be loaded using a pH change system. In such a process, polymer is dispersed in aqueous liquid in ionised form, in which it solubilises at relatively high concentrations without forming micelles. Subsequently the pH is changed such that some or all of the ionised groups become deprotonated so that they are in non-ionic form. At the second pH, the hydrophobicity of the block increases and micelles are formed spontaneously.

Where the block copolymer is temperature sensitive such that micelles form reversibly at a critical temperature, the loading process may involve a temperature change around the transition temperature. Micelles may be loaded by contacting the empty micellar composition with biologically active, either in solid form or in dissolved form in an organic solvent. Solvent may optionally be removed in a subsequent step, e.g. by evaporation. It is found that loading of a model hydrophobic drug from a film on the inner surface of a vessel containing the empty polymer micelles generated micellised drug after reasonable periods.

There follows a list of drugs for which the present invention may be useful with values for the log P, calculated using the log Pcalculator at daylight.com and as determined experimentally, where the information is available, are listed below. Drugs having log P (i.e. determined experimentally) or clog P (i.e. recalculated) greater than 1.0, preferably greater than 1.5 or 2.0 are particularly suitable.

| Drug | Log P (calc) | Mw | LogP (Exp) | Reference |
|---|---|---|---|---|
| Actinomycin | | 1255.44 | 0.997 | |
| Angiopeptin | 3.61 | 1009.23 | | |
| Aspirin | | 180.16 | 1.23 | Hansch J Org Chem 32/2583/1967 |
| Atorvastatin | | 558 | 1.61 | |
| Batimastat | 2.446 | 477 | | |
| Carmofur | | | 2.63 | |
| Carmustine | | | | |
| Carvedilol | 4.041 | 406 | | |
| Cerivastatin | | 459 | 2.05 | |
| Cilostazol | | 369 | 2.3 | |
| Dexamethasone | | 392.5 | 1.83 | Hansch et al 1995 |
| Dipyramidole | 2.532 | 504.63 | | |
| Doxorubicin | 1.04 | 580 | | |
| Estradiol | | 272.39 | 4.3 | Acta Pharm Suec 16/151/1979 |
| Etoposide | | 588.6 | 0.99 | Pharmaceutical Research 6/5/408/1989 |
| Fluorodeoxyuridine | | | −1.16 | |
| Fluorouracil | | 130 | −1 | |
| Fluvastatin | | 411 | 1.67 | |
| Gemcitabine | 0.834 | 263 | | |
| Irinotecan | 2.521 | 622 | | |
| Leflunomide | 2.2227 | 270 | | |
| L-Leucovirin | −3.2 | | | |
| Lomustine | 2.14 | | | |
| Lovastatin | | 404 | 1.7 | |
| Marimastat | 0.756 | 331 | | |
| Methylprednisolone | 1.42 | 374.5 | | |
| Methotrexate | | 454 | −1.8 | Pharmaceutical research 7/7/712/1990 |
| Mitomycin C | −3.221 | | | |
| Mitoxantrone | 0.239 | | | |
| Orange OT | 4.01 | 262 | | |
| Pravastatin | | 424 | −0.23 | |
| Prinomastat | 2.93 | 411 | | |
| Rapamycin | 7.76 | 914.2 | | |
| Roxithromycin | 2.04 | 837.06 | | |
| Simvastatin | | 418 | 2.06 | |
| Taxol | | 853.9 | 3.98 | J. Pharm Sci 85/2/228/1996 |
| Taxotere | 5.86 | | | |
| 6-Thioguanine | | 167 | −0.28 | |
| Tirofiban | 0.46 | 440.6 | | |
| Topotecan | 1.757 | 421 | | |
| Tranilast | −1.09 | 327.3 | | |
| Vinblastine | | 814 | 1.68 | Cancer Chemother Pharmacol 26/4/263/1990 |
| Vincristine Sulfate | | 923 | 2.14 | Cancer Chemother Pharmacol 26/4/263/1990 |

Micellised drug delivery systems have been used for cytotoxic drugs, for instance used in anti-cancer and/or anti-angiogenic therapies, and such drugs may be used in the present invention. Examples are doxorubicin, daunomycin and paclitaxel and analogues and derivatives thereof.

The invention is illustrated in the accompanying examples.

EXAMPLE 1

A-B block copolymers were formed by an atom transfer polymerisation with MPC being homopolymerised in a first block forming step using an oligo(ethylene glycol) initiator as described by Ashford E. J. et al in Chem. Commun. 1999, 1285 (the reaction product of monomethoxy-capped oligo (ethylene glycol) and 2-bromoisobutyryl bromide) in the presence of bipyridine ligand and copper (I) bromide catalyst dialkylaminoalkyl methacrylate (either DEA (diethylaminoethyl methacrylate or DPA, 2-(di-isopropyl-amino)

ethylmethacrylate)) was polymerised in a second block forming step. The degree of polymerisation for each block and the second monomer are indicated in Table 1.

The reaction conditions were [MPC]=2.02M (6.0 g in 10 ml methanol), [MPC]:[OEG-Br]:[CuBr]:[bipy]=(30 or 20 as shown in Table 1):1:1:2, T=20° C.; MPC was polymerised first in all cases to about 120 minutes followed by addition and polymerisation of an appropriate amount of neat DEA. Almost complete monomer conversion was achieved about 20 hours for the diblock, as indicated by $^1$H NMR spectroscopy (no residual vinyl double bonds). The reaction mixture was diluted with methanol and passed through a silica column to remove residual ATRP catalyst. After solvent evaporation, the products were dried under vacuum at room temperature. The molecular weight and polydispersities were determined by aqueous gel permeation chromatography and the results are shown in Table 1.

TABLE 1

Data of the polymerization of MPC - amine diblock copolymers in methanol

| EX # | Comonomer | MPC in copolymer (mol %) | Target Dp MPC:amino | Mn (AGPC) MPC Diblock | Mw/Mn MPC Diblock |
|---|---|---|---|---|---|
| 1 | DEA | 50 | 20:20 | 10000 | 1.22 |
| 2 | DEA | 33 | 10:20 | 7000 | 1.29 |
| 3 | DEA | 50 | 30:30 | 16000 | 1.30 |
| 4 | DEA | 33 | 30:60 | 24000 | 1.29 |
| 5 | DEA | 23 | 30:100 | 32000 | 1.28 |

AGPC = aqueous gel permeation chromatography

EXAMPLE 2

Block Copolymer Preparation by the Macroinitiator Route

Relatively monodisperse macroinitiators of a variety of different hydroxy-terminated polymers can be made by reaction of the terminal OH with 2-bromoisobutyryl bromide according to (scheme 1).

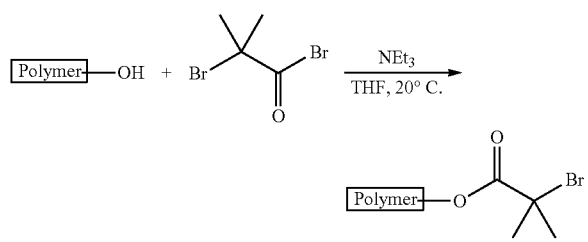

Where Polymer—OH is PEO—OH, PPO—OH or PDMS—OH

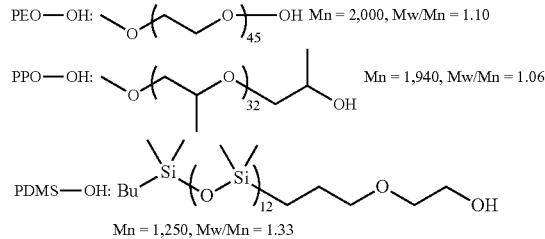

The resulting macroinitiators are used in the synthesis of block copolymers (examples shown in Table 2) by the method outlined in Example 1. The components were used in amounts as follows MPC(6.0 g, 2.02×10$^{-2}$ mol). The molar ratios of MPC: initiator: Cu(I)Br:bpy was x:y:1:7 where x and y are given in Table 2. The solvent used is indicated in Table 2.

TABLE 2

Examples of Block Copolymers Using the Macroinitiator Route

| Target Composition | Solvent Composition | [Macroinitiator] (mol × 10$^{-4}$) | Reaction Time (h) | Residual Cu By ICP-AES/ ppm |
|---|---|---|---|---|
| PEO$_{45}$-MPC$_{40}$ | MeOH | 5.05 | 24 | 2.0 |
| PEO$_{45}$-MPC$_{10}$ | MeOH | 1.35 | 3 | 1.5 |
| PPO$_{33}$-MPC$_{20}$ | MeOH | 0.10 | 3 | 2.5 |
| PPO$_{33}$-MPC$_{30}$ | MeOH | 6.73 | 20 | 3.1 |
| PPO$_{33}$-MPC$_{50}$ | IPA | 4.2 | 23 | 2.9 |
| PPO$_{33}$-MPC$_{100}$ | MeOH | 2.10 | 24 | 3.2 |
| PDMS$_{13}$-MPC$_{100}$ | 4:1 MeOH:IPA | 1.35 | 25 | 2.7 |
| PDMS$_{13}$-MPC$_{50}$ | 4:1 MeOH:IPA | 0.04 | 23 | 1.5 |
| PDMS$_{13}$-MPC$_{30}$ | 4:1 MeOH:IPA | 6.73 | 23 | 1.8 |

EXAMPLE 3

Temperature-induced Micellisation of Diblock Copolymers

Diblock copolymers in which the hydrophobic block is composed of PPO or DMA have been shown to undergo temperature-induced micellisation by $^1$H NMR. FIG. 1 shows the proton NMR spectra from 0.8 to 1.8 ppm of MPC50-PPO$_{33}$ with increasing temperature from 5-70° C. Note that the peaks characteristic of the PPO (a) decrease in size and broaden into two, with increasing temperature, whilst that of the MPC backbone moves from a broad, undefined hump, to a more well defined et of peaks. This illustrates that as the temperature is raised, the PPO becomes more hydrophobic and moves to the core of the forming micelles, and vice versa for the MPC, which is in the more solvated outer shell of the micelle structure.

Figure 2:
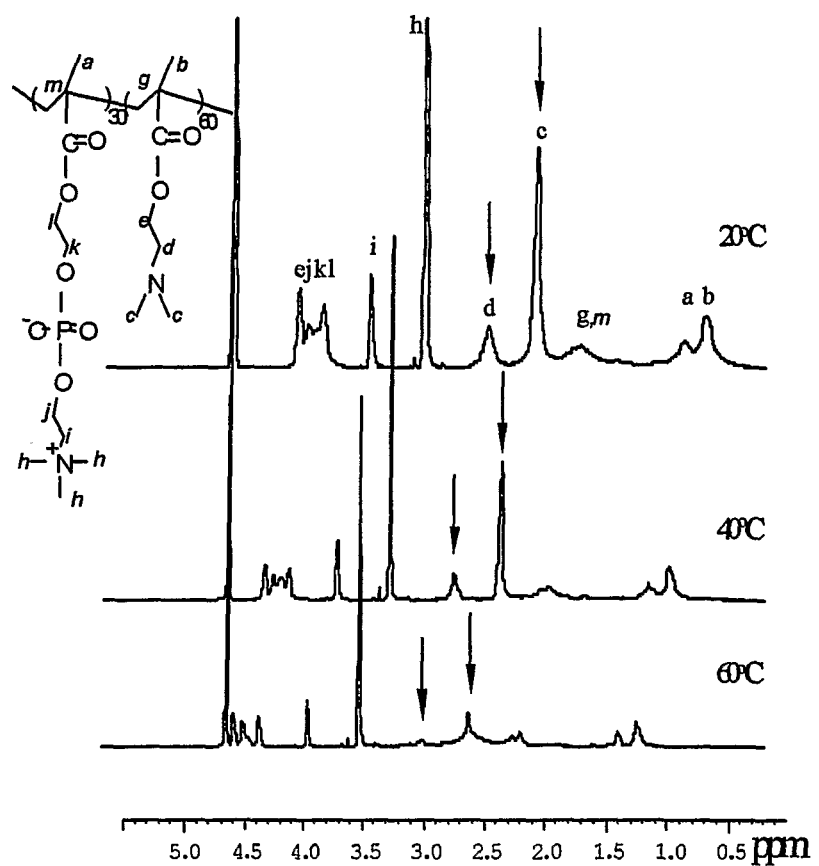

Likewise for the case of the MPC30-DMA60 copolymer, from the spectra in FIG. 2 the peaks characteristic of the DMA (c & d) are seen to disappear with increasing temperature, as they form the central core of the forming micelles.

EXAMPLE 4 pH-Induced Micellisation of Diblock Copolymers

One of the blocks of the diblock may be composed of a species of tunable hydrophobicity, for instance a tertiary amine group that can be protonated or deprotonated. For these materials, a pH-induced micellisation can be observed shown schematically in FIG. 3.

Evidence for this phenomenon can be seen from the proton NMR of MPC30:DPA60 copolymer at different pHs. From the NMR spectra at different pH is shown in FIG. 4 it can be see that the peaks corresponding to the pH-tunable block disappear as they move into the core of the micelle at high pH.

EXAMPLE 5

Studies of Model Drug Entrapment by Diblock Copolymers

The dye Orange OT was used as a model compound for assessing entrapment and loading capacities. McIlvaines buffer was prepared according to Documenta Geigy to the required pH using the formula: x ml A+(100−x) ml B, where A was 0.1M citric acid (BDH Merck) and B was 0.2M disodium phosphate (BDH Merck). For pH 4, x=61.45, for pH 8, x=2.75. All solutions were filtered with 0.2 mm syringe filters (Nalge Nunc) to remove any particulate contamination. 40 µl of 0.1% w/v Orange OT (Aldrich) in ethanol (BDH Merck) was dried down into the individual wells of a 96 well assay plate (Bibby Sterilin), leaving a film of Orange OT on the bottom of each well. The polymers tested were dissolved in McIlvaines buffer at pH 4, and the pH then raised to the desired pH by addition of 5M NaOH (Aldrich). The volume then topped up with McIlvaines buffer of the same pH, to give a final known concentration of polymer stock solution. A series of halving dilutions of the prepared polymer stock solution were prepared, using McIlvaines buffer of the same pH. 160 µl of each dilution was aliquoted out into the individual wells of the prepared 96 well plates, using repeats of n=6. Blank controls of McIlvaines buffer at the same pH were run alongside to zero the plate. These were incubated at the desired temperature (4 or 37° C.) for 18 hours. The samples were then transferred to fresh clean 96 well assay plates, and the absorbance at 492 nm measured using a Microtek 96 well plate reader (ICN FLOW).

To determine the peak absorbance wavelength for Orange OT, and whether the pH of the solution had an effect on the absorbance 2 mg of Orange OT was dissolved in 30 ml of 40% ethanol in water. This was then filtered to remove undissolved Orange OT. The pH was adjusted by addition of diluted HCl (Aldrich) and NaOH (Aldrich), and the absorbance scanned from 900 nm to 180 nm against a 40% ethanol in water blank, using a Perkin-Elmer Lambda 2 UV/Vis spectrophotometer.

To determine the maximum amount of Orange OT solubilised, and allow conversion to a mol:mol (dye:polymer) ratio, 40 µl of the 0.1% w/v Orange OT in ethanol was diluted with 120 µl ethanol, and the maximum absorbance at 492 nm measured using the 96 well plate reader, making further dilutions with ethanol where necessary. To examine a possible variation in maximum absorbance at 492 nm between the Orange OT dissolved in ethanol and Orange OT entrapped in micelles, a control assay was conducted. The dye entrapment assay was repeated, but with the polymer in pH adjusted water, to allow for dilution with ethanol. A single concentration of polymer was, with no dilutions. Once the polymer with entrapped Orange OT had been recovered, half of the samples were diluted 50% with water of the same pH, whilst the remaining half were diluted with 50% with ethanol, and the absorbance at 492 nm measured using clean 96 well plates and the 96 well plate reader.

Figure 5:
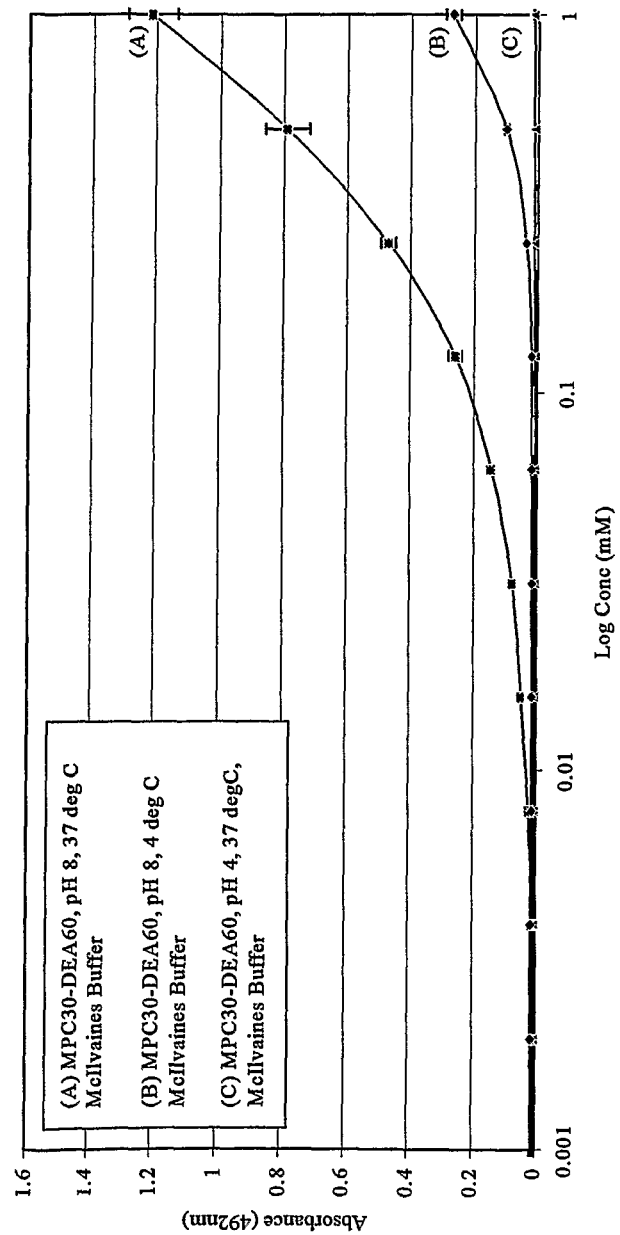
FIGS. 5 to 7 shows the results of Example 5.
Figure 6:
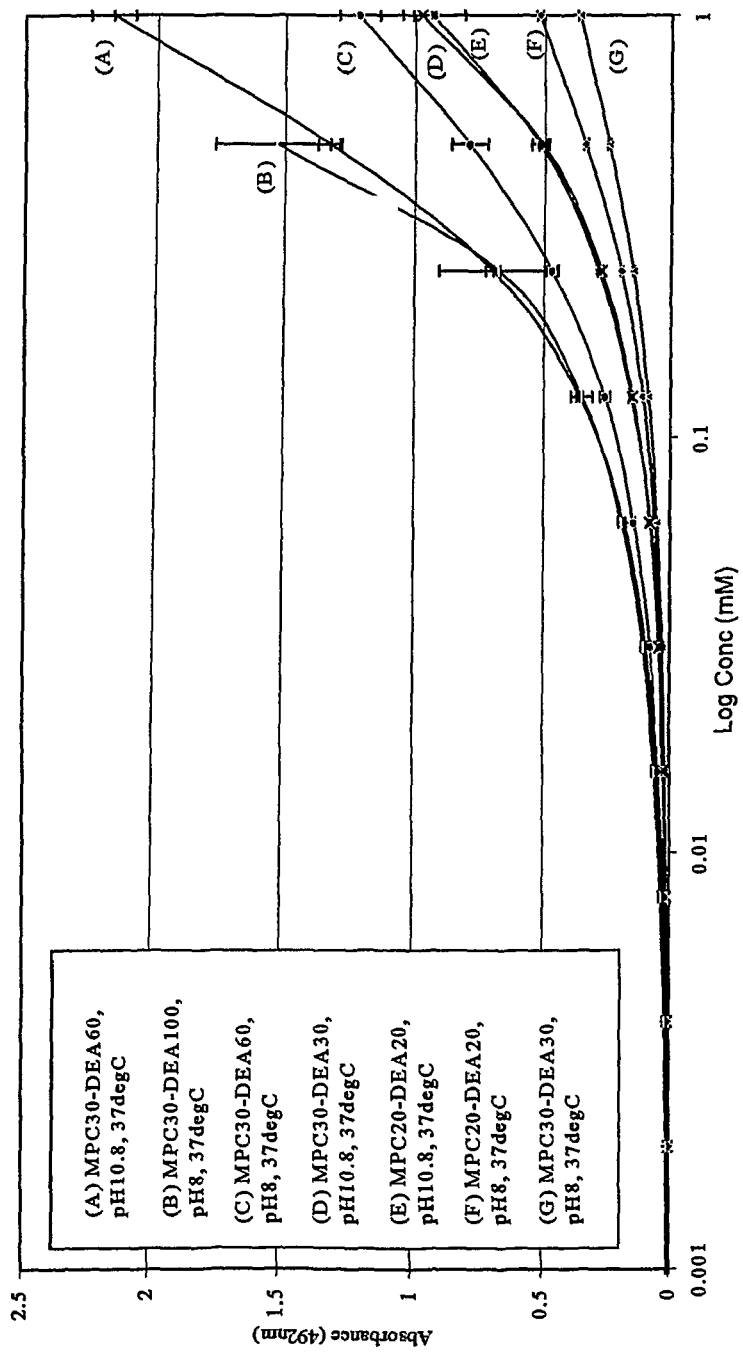

FIG. 5 shows show the dye uptake profile with concentration for MPC30-DEA60. The results indicate that at pH 4 at 37° C. (C) there was no dye solubilisation, whilst at pH 8 at 37° C. (A) there was dye uptake. This supports the idea that the MPC-DEA block copolymers are in a unimer form at low pH and in the micelle form at high pH. Also of interest in FIG. 5 was the apparent temperature effect, as it can be seen that at pH 8 and 4° C. (B) the level of dye solubilisation was greatly reduced in comparison to pH 8 at 37° C. A comparison of the results for all the MPC-DEA block co-polymers at pH 8 and pH 10.8, at 37° C. in McIlvaines buffer, can be seen in FIG. 6. This shows that by increasing the hydrophobicity of the co-polymers, either by increasing DEA block length or raising the pH, that the amount of hydrophobic Orange OT dye uptake is also increased.

Figure 7:
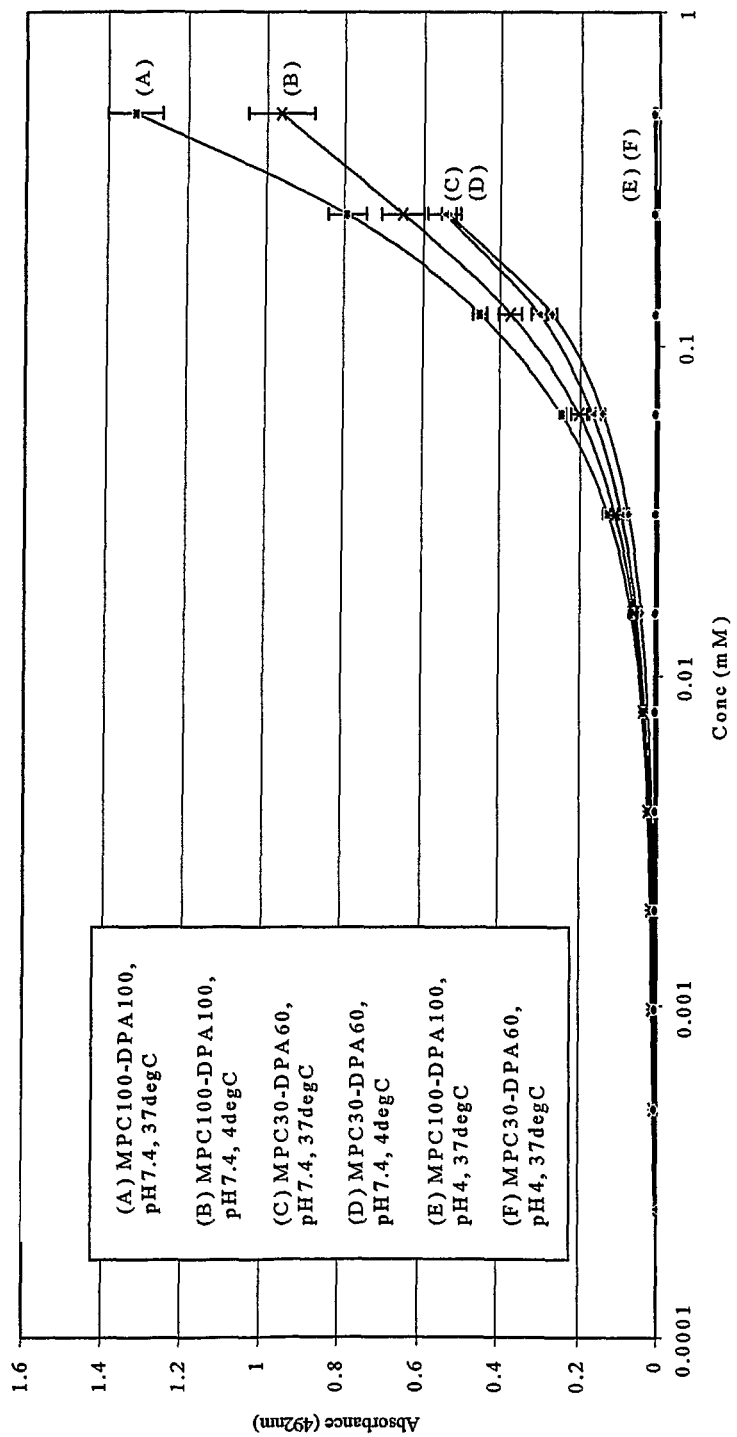

The results for the MPC-DPA block co-polymers can be seen in FIG. 7 and it can be seen that the same curvature and non-distinct CMC as seen for the MPC-DEA polymers is present. At pH 4 at 37° C. there is no dye uptake, whilst at pH 7.4 at 37° C. solubilisation of the dye has taken place. This again supports the polymers being in unimer form at low pH and micelles at high pH. The results suggest that the MPC-DPA polymers are thermally stable, as the MPC30-DPA60 results for pH 7.4 at 4° C. show very little difference to those at 37° C. The amount of dye uptake is again raised when the hydrophobicity of the polymers is increased, by increasing the DPA block length.

EXAMPLE 6

Dye Loading Capacity Studies

Figure 8:
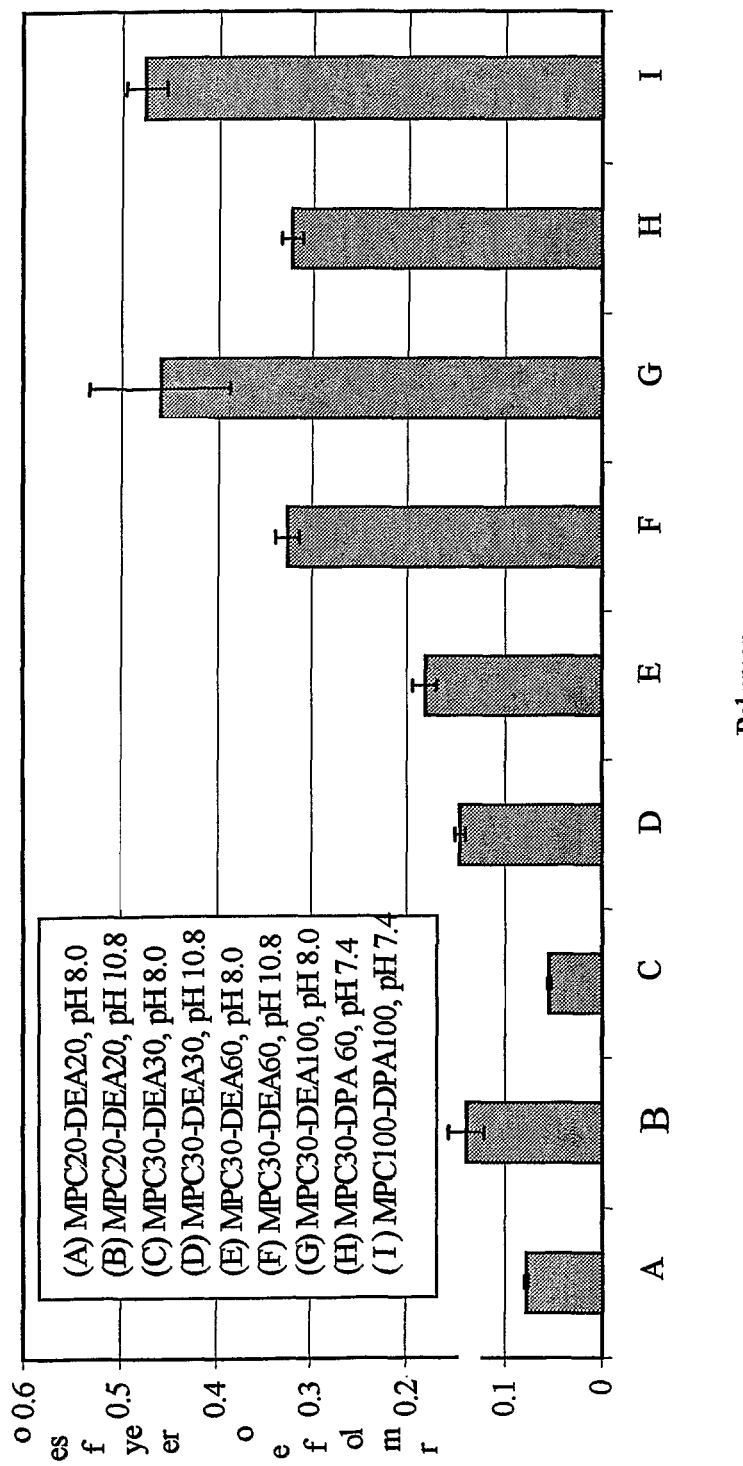
FIG. 8 shows the results of Example 6.

Following determination of the maximum amount of Orange OT that could be solubilised by the polymers in the dye entrapment assay, the results for the MPC-DEA and MPC-DPA polymers were converted to a mol:mol ratio. The mol:mol ratio of dye to polymer can be seen in FIG. 8 and it can be seen that the ratio of dye to polymer increases as the pH of the solutions is increased, and as the hydrophobic block (DEA or DPA) is increased in length. The lowest ratio belonged to MPC20-DEA20, with the highest being the MPC 100-DPA100. The test are all carried out at 37° C.

EXAMPLE 7

Particle Size Analysis of the Diblock Copolymer Micelles

The particle diameter of the MPC-DEA and MPC-DPA polymers was measured using photon correlation spectroscopy (PCS) with a 10 mW He—Ne laser, a wavelength of 63 nm, and a 90 degree detector angle to the laser. Initial work focused on the MPC-DEA polymers, examining particle size in response to pH and temperature. Following the finding that MPC-DEA polymers were not in the micelle form at pH 7.4, the focus was switched to the MPC-DPA polymers which had a more favourable pH profile. The particle diameter (nm) at 5° C., 25° C., and 70° C. for MPC-DEA and MPC-DPA at a number of different pH values can be seen in Tables 3-5. At the foot of each Table the percentage of micelles and aggregates are given for the indicated samples.

TABLE 3

| | Particle Diameter (nm) | | | | |
| --- | --- | --- | --- | --- | --- |
| | NO DYE | | | | |
| | pH | pH | pH | pH | pH |
| 5° C. | 4.0 | 7.4 | 8.0 | 10.8 | 12.0 |
| MPC-DEA | | | | | |
| 10-20 | | | 8 | 10 + 22 (a) | 9 + 21 (b) |
| 20-20 | 5 | | 8 | 15 | 16 |
| 30-30 | 7 | | 8 | 8 + 22 (c) | 10 + 24 (d) |
| 30-60 | 7 | 7 + 37 (e) | 9 + 34 (f) | 9 + 35 (g) | |
| 30-100 | 9 | 8 + 38 (h) | 41 + 152 (i) | 46 + 208 (j) | |

TABLE 3-continued

| 5° C. | Particle Diameter (nm) | | | | |
|---|---|---|---|---|---|
| | NO DYE pH 4.0 | pH 7.4 | pH 8.0 | pH 10.8 | pH 12.0 |
| MPC-DPA | | | | | |
| 30-60 | 10 | 44 | | | |
| 100-100 | 12 | 33 | | | |

(a) 75% + 25%
(b) 49% + 51%
(c) 86% + 14%
(d) 82% + 18%
(e) 84% + 16%
(f) 67% + 33%
(g) 57% + 43%
(h) 62% + 38%
(i) 93% + 7%
(j) 94% + 6%

TABLE 4

| 25° C. | Particle Diameter (nm) | | | | |
|---|---|---|---|---|---|
| | NO DYE pH 4.0 | pH 7.4 | pH 8.0 | pH 10.8 | pH 12.0 |
| MPC-DEA | | | | | |
| 10-20 | | 10 | 21 | 22.0 | 25 |
| 20-20 | 7 | 12 | 21 | 22 | 23 |
| 30-30 | 8 | 13 | 7 + 29 (a) | 25 | 2 |
| 30-60 | 9 | 14 | 26 | 29 | 29 |
| 30-100 | 9 | 15 | 34 | 47 | 48 |
| MPC-DPA | | | | | |
| 30-60 | 9 | 43 | | | |
| 100-100 | 12 | 33 | | | |

(a) 97% + 3%

TABLE 5

| 70° C. | Particle Diameter (nm) | | | | |
|---|---|---|---|---|---|
| | NO DYE pH 4.0 | pH 7.4 | pH 8.0 | pH 10.8 | pH 12.0 |
| MPC-DEA | | | | | |
| 10-20 | | | 30 | 25 | 27 |
| 20-20 | 6 | | 25 | 24 | 27 |
| 30-30 | 8 | | 26 | 24 | 25 |
| 30-60 | 7 | | 26 | 30 | 32 |
| 30-100 | 9 | | 38 + 165 (a) | 210 | 189 |
| MPC-DPA | | | | | |
| 30-60 | 9 | 44 | | | |
| 100-100 | 12 | 38 | | | |

(a) 98% + 2%

In Table 3 it can be seen that at pH 4.0, 5° C., both the MPC-DEA and MPC-DPA polymers are in their unimer form, as indicated by the small particle size. When the pH of the MPC-DPA polymers was increased to pH 7.4, the particle size increased, indicating micelle formation, and no low temperature effect. However, when the pH of the MPC-DEA polymers was increased to pH 8.0, the smaller block ratio polymers remained in unimer form, whilst the larger block ratio polymers had a mixture of unimers and micelles, the relative percentage of unimers and micelles can be seen in the lower block of Table 2. Further increases in pH to 10.8 and 12.0 saw the lower block ratio MPC-DEA polymers also shift to a mixed unimer and micelle system, with the % of micelles increasing as the pH and DEA block length increased. The only exception to this being MPC20-DEA20, which appears to be of an intermediate particle size. It is clear when Table 3 is compared to Table 4 that the lower temperature of 5° C. prevented complete micelle formation within the systems.

In Table 4 it can be seen that at pH 4.0, 25° C., both the MPC-DEA and MPC-DPA polymers are in their unimer form, as indicated by the small particle size. At pH 7.4 the MPC-DEA polymers had not completed micellisation, and whilst larger than the unimers of pH 4.0, it was not until pH 8.0 and above that the micelles had formed. The MPC30-DEA30 at pH 8.0 was still in the mixed unimer/micelle system, the percentage of unimers and micelles, as shown at the bottom of Table 4, indicates the MPC30-DEA30 pH 8.0 system was predominately unimers. In contrast to the MPC-DEA polymers, the MPC-DPA polymers formed micelles at pH 7.4 and above, with no unimer presence.

In Table 5 it can be seen that at pH 4.0, 70° C., both the MPC-DEA and MPC-DPA polymers are in their unimer form, as indicated by the small particle size. The MPC-DPA polymers formed micelles at pH 7.4, and the MPC-DEA polymers formed micelles at pH 8.0 and above. The MPC30-DEA100 at pH 8.0 formed a mixed system of micelles and larger aggregates, and at pH 10.8 and 12.0 the micelles has formed large aggregates. This is likely to have been due to the high temperature increasing the hydrophobicity of the DEA block and thus forcing the polymer out of solution. When Tables 3 to 5 are compared, it is clear that the MPC-DPA polymers are temperature stable, whilst the MPC-DEA polymers are temperature sensitive with low temperature reducing micellisation.

EXAMPLE 8

Release of Model Drug from Micelles

Figure 9:
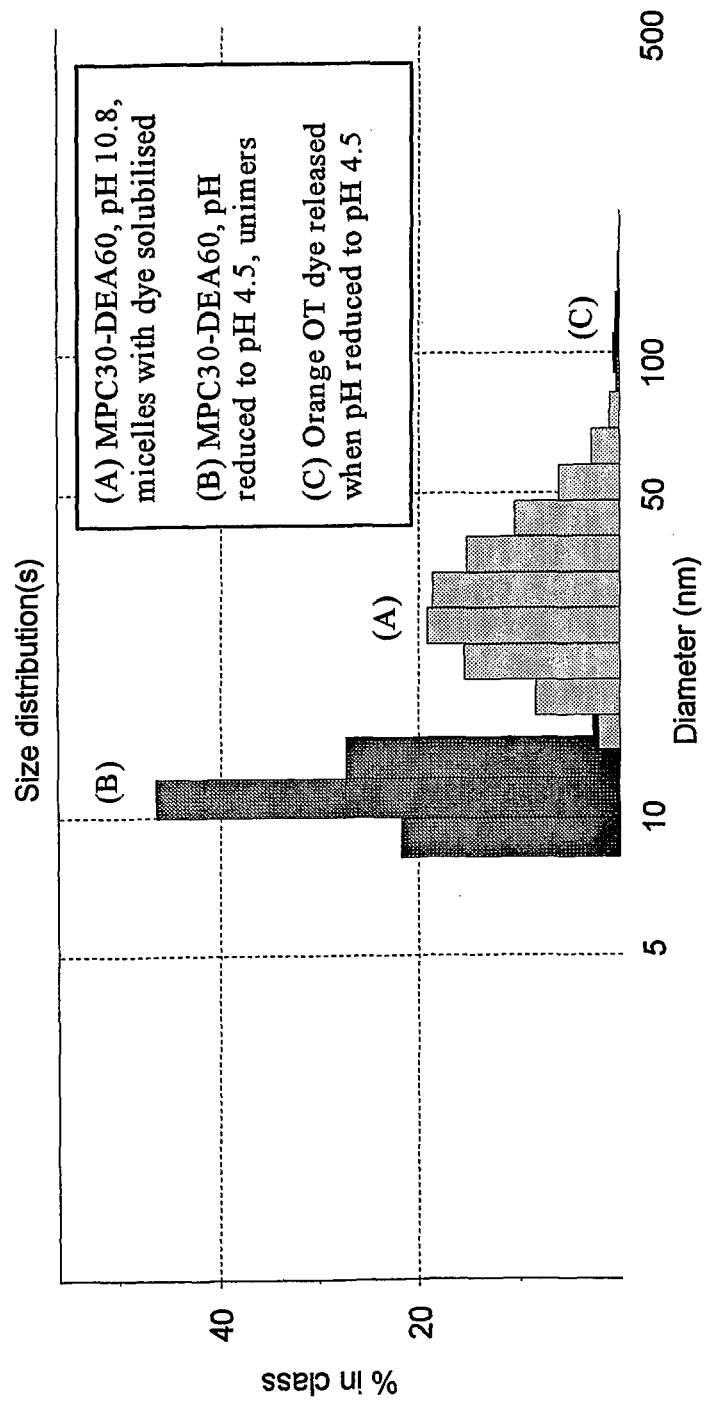
FIG. 9 shows the results of Example 8.

The release of solubilised Orange OT dye from micelles, as a model for drug release, using lowered pH as the stimuli was examined. MPC30-DEA60 micelles with Orange OT dye solubilised, in McIlvaines buffer at pH 10.8 at 25° C., disassembled to polymer unimers and insoluble dye aggregates when the pH was reduced to pH 4.5, as seen in FIG. 9. The micelles with the dye solubilised had a mean particle diameter of 34 nm at pH 10.8. The unimers had a mean particle diameter of 10 nm, whilst the released dye aggregates had a mean particle diameter of 113 nm. At pH 4.5 the unimers represented 99% of the population, and the dye aggregates 1% of the population.

EXAMPLE 9

Temperature, pH and Dilution Effects on Particle Size

Figure 10:
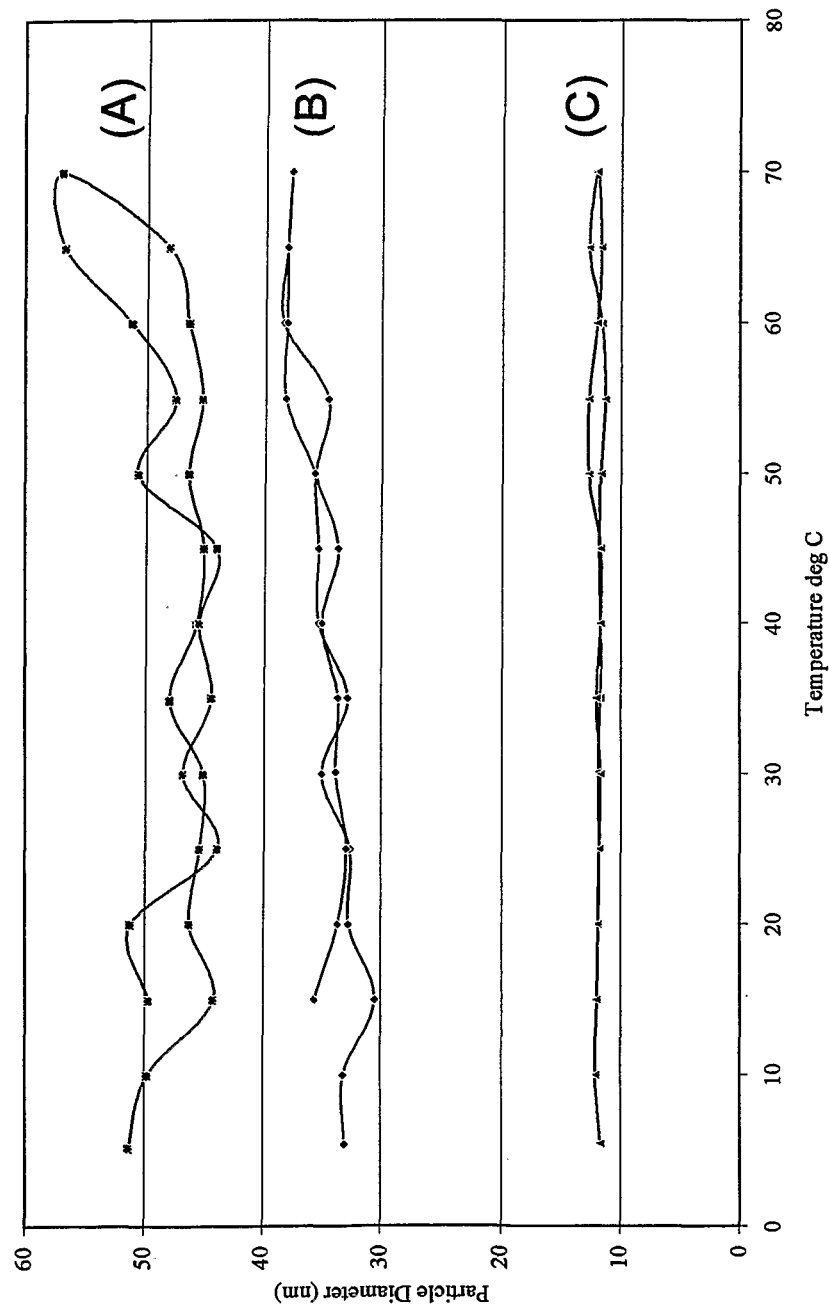
FIGS. 10 to 12 shows the results of Example 9.

To further examine the thermal properties of the MPC-DPA polymers, particle diameter measurements at temperatures ranging between 5° C. and 70° C., at 5° C. intervals where undertaken. The results for MPC100-DPA100 can be seen in FIG. 10, and show that MPC100-DPA100 forms a temperature stable micelle system. At pH 4.0 the system is stable and in unimer form from 5° C. to 70° C. At pH 7.4 the MPC100-DPA100 is in micelle form and is also stable across the temperature range, and when Orange OT dye was solubilised the particle size increased and continued to be stable from 5° C. to 70° C.

Figure 11:
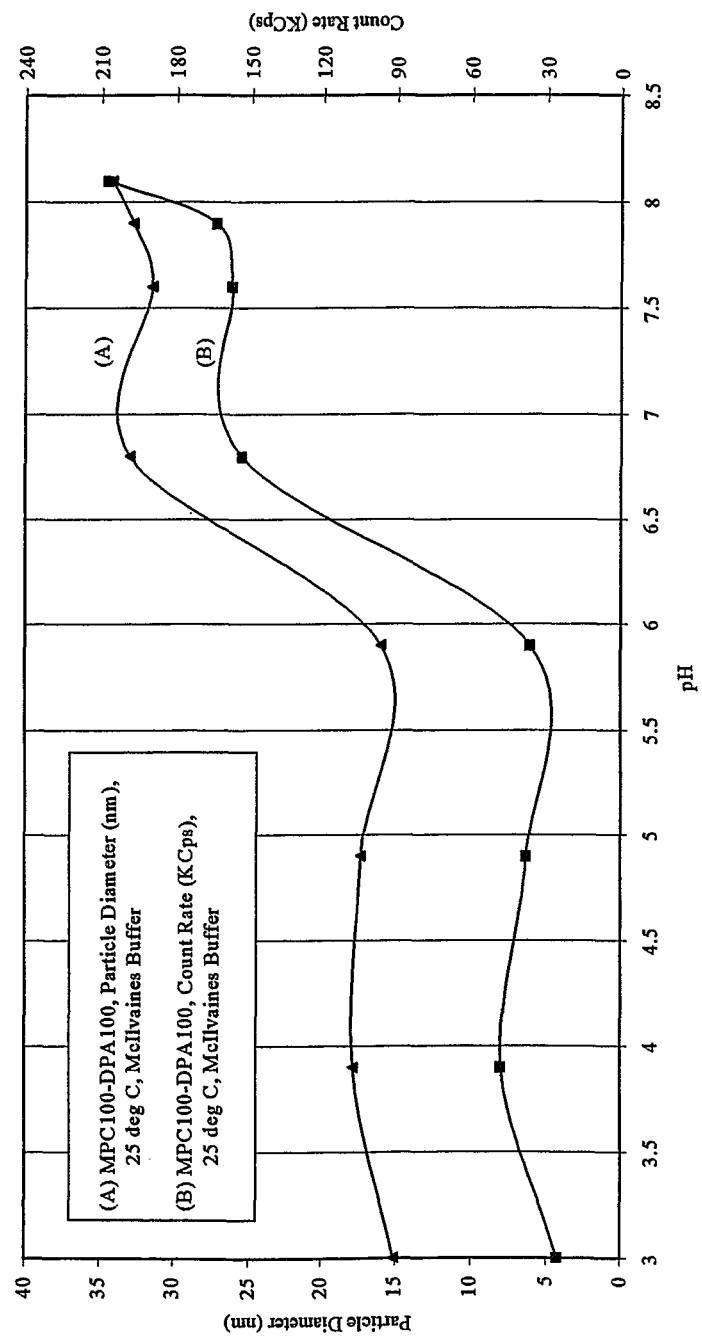

To examine the pH response profile of the MPC-DPA polymers, solutions at pH values between pH 3.0 and 8.5 were prepared and the particle diameter measured using PCS. The results for MPC100-DPA100 are shown in FIG. 11, the pH response is sharper than that of MPC30-DPA60, with micellisation beginning at about pH 6.0 and complete by pH 7.0, as indicated by the increasing particle diameter and count rate. The particle size at pH 7.4 is consistent with that indicated at 25° C. in Table 5 and FIG. 10.

Figure 12:
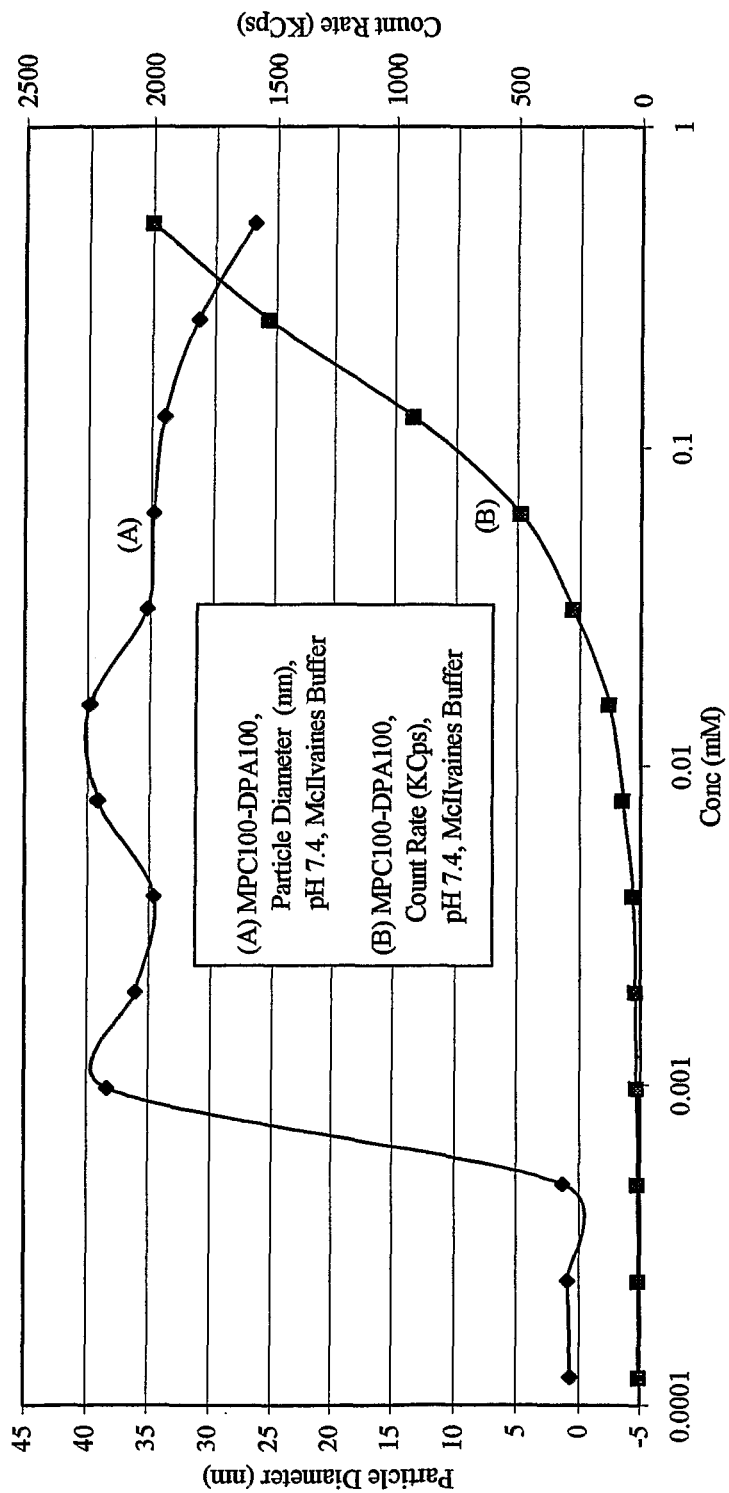

The dilution stability of the micellised polymers was monitored using PCS, by preparing the MPC-DPA polymers in McIlvaines buffer, pH 7.4, and measuring the particle diameter of sequential halving dilutions at 25° C. Upon each dilution the number of micelles present was halved, as is evident from the count rate which can be seen to halve each time in FIG. 12. MPC100-DPA100 micelles were present down to 0.001 mM concentration (as was also the case for MPC30-DPA60, data not shown), as seen in FIG. 12. It may be that the micelles disassembled at 0.001 mM concentration; alternatively the limit of detectability using PCS may have been reached. 0.001 mM does however correspond with the lower end of the curving CMC graph for MPC-DPA polymers as seen in FIG. 7.

EXAMPLE 10

Imaging of the Particles

Figure 13:
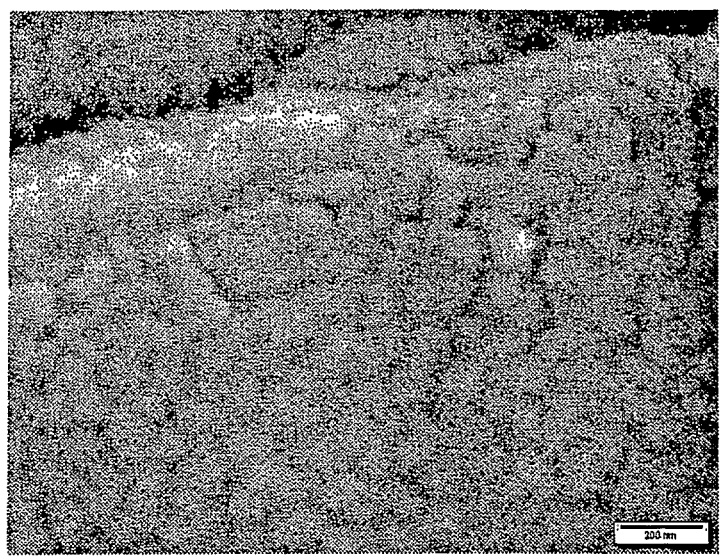
FIGS. 13 and 14 show the results of Example 10.
Figure 14:
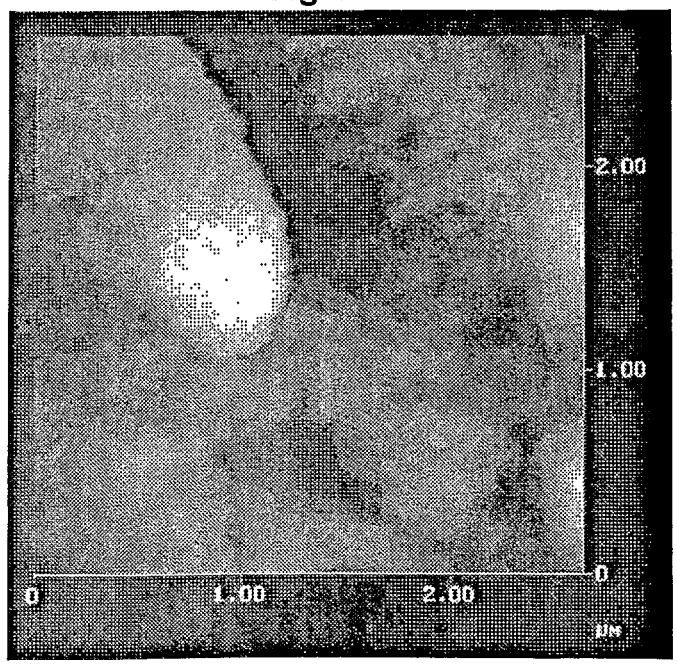

The polymer MPC30-DEA60 at pH 12.0 in water was imaged using Cryo-SEM, and tapping mode AFM. The Cryo-SEM image can be seen in FIG. 13 (in which the bar in the lower right corner is 200 nm), a mixed particle population of approximate diameter 50 nm to 100 nm can be seen. The height phase tapping mode AFM image can be seen in FIG. 14, particle diameter appears to be predominately of approximately 100 nm (in this figure the scale on the x axis has divisions of 1 μm). A subsequent PCS measurement of the sample solution gave a particle diameter of 28.2 nm. The larger particle size indicated by AFM and Cryo-SEM imaging may be the result of the sample preparation for each technique.

EXAMPLE 11

Cell Cytotoxicity Assessment

Figure 15:
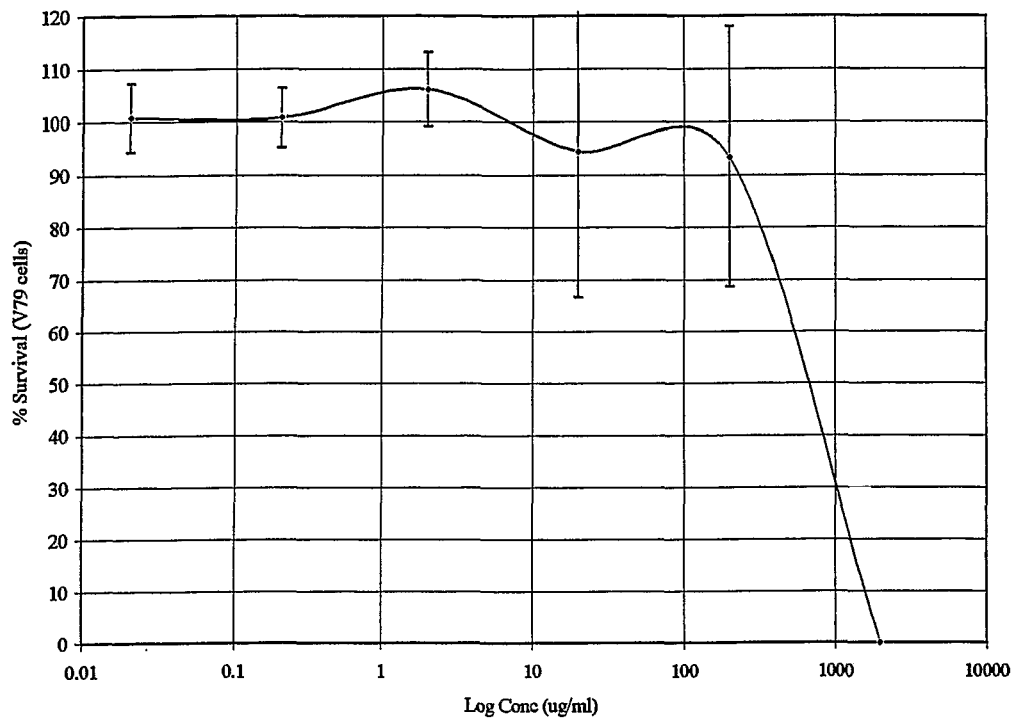
FIGS. 15 to 17 show the results of Example 11.
Figure 16:
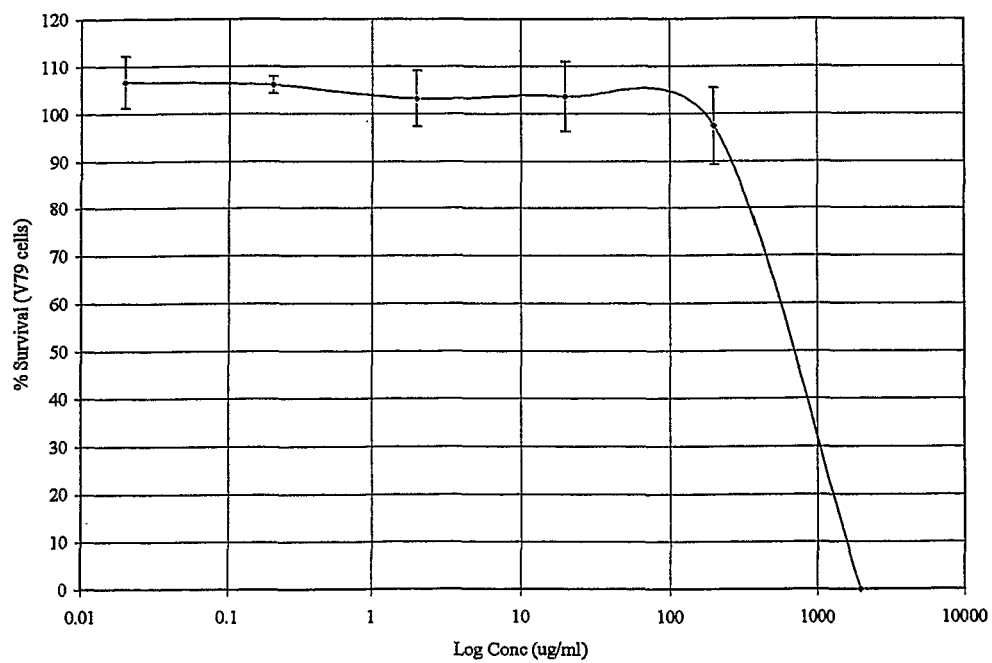
Figure 17:
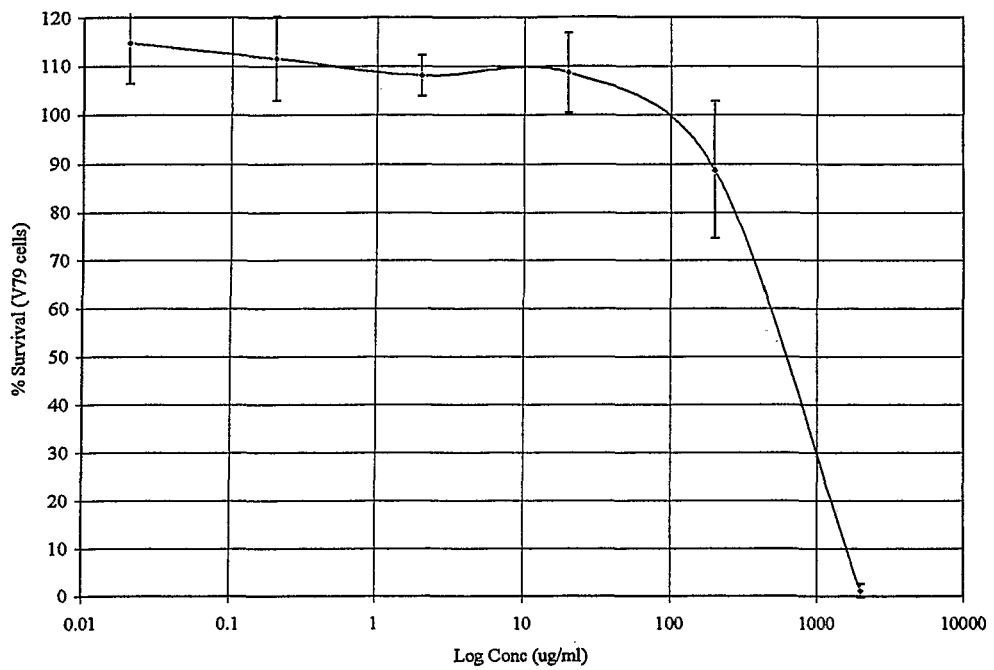

To determine potential cellular toxicity of the MPC-DPA polymers, V79 cell based colony formation cytotoxicity assay was used. The test was carried out at 37° C. in DMEM with 2.5% FCS and 1% penstrep P/S. The results from a blank plate of media provided the 100% survival figure, from which the % survival can be calculated for each of the dilutions of the MPC-DPA polymers, and the $EC_{50}$ determined. The results for MPC30-DPA60, at pH 7.4 in PBS, can be seen in FIG. 15, and the $EC_{50}$ is 650 μg/ml. The results for MPC100-DPA100, at pH 7.4 in PBS, can be seen in FIG. 16, and the $EC_{50}$ is 700 μg/ml. FIG. 17 shows the results for a control of PBS without the polymer, the $EC_{50}$ is 600 μg/ml, demonstrating that the $EC_{50}$ of the MPC-DPA polymers was the result of the first 50% buffer to media dilution of the assay.

EXAMPLE 12

Surface Tension Determinations

The surface tension of solutions of various diblock copolymers were determined using a Kruss K12 tensiometer. These determinations were made under various pH conditions in order to examine the relative surface activity of the various diblock copolymers.

Figure 18:
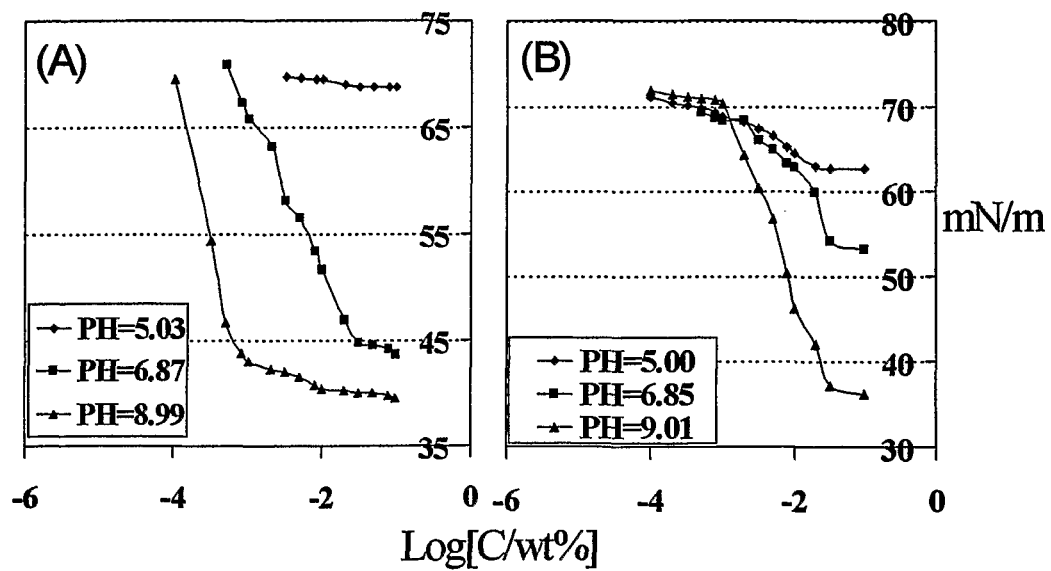
FIGS. 18a and 18b show the results of Example 12.

FIGS. 18a and b show typical plots obtained for both a DMA (a) and DEA (b) system. FIG. 18a shows the results for MPC30-DMA60 and FIG. 18b shows the results for MPC30-DEA60. Clearly, the diblock copolymers show no effect on surface activity at low pH, as the amine groups are protonated and the polymers molecularly soluble in water. At higher pH, the amine groups deprotonate, the amine-containing block becomes more hydrophobic and the polymer shows surface activity, as demonstrated by the drop in surface tension with increasing concentration of the polymer in solution.

EXAMPLE 13

Pyrene Partition Experiments

Figure 19:
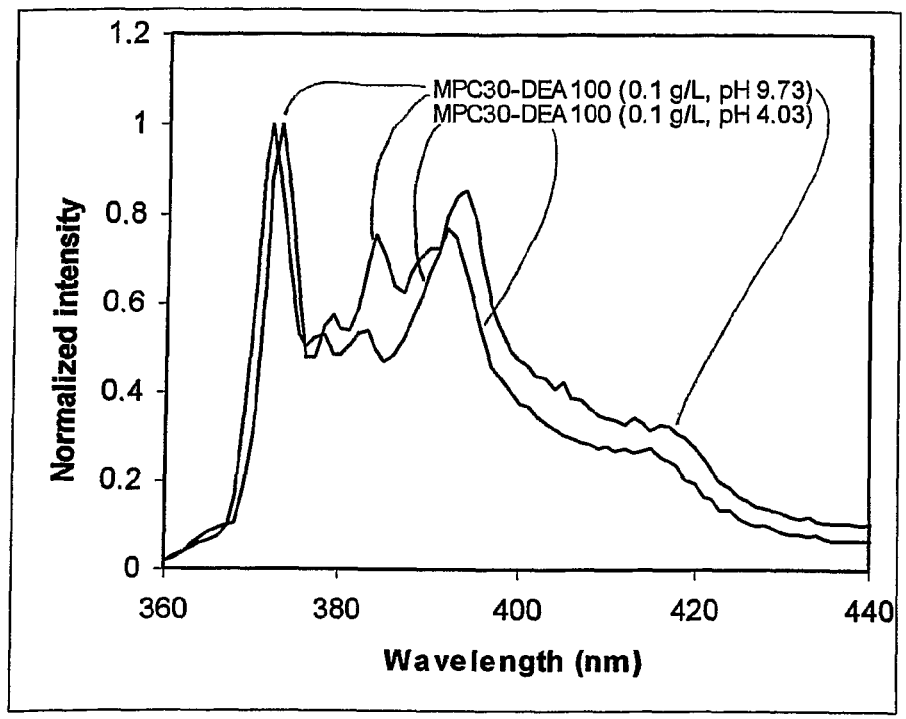
FIGS. 19 and 20 show the results of Example 13.

The $MPC_{30}$-$DMA_{60}$, $MPC_{30}$-$DEA_{60}$ and $MPC_{30}$-$DPA_{60}$ diblocks were molecularly dissolved in turn in doubly-distilled water at pH 2. Pyrene/copolymer solutions were prepared by adding acetone solutions of pyrene into dry 10.0 ml volumetric flasks. After evaporation of the acetone, diluted copolymer stock solutions were added so as to obtain final copolymer concentrations ranging from $1 \times 10^{-4}$ to 5.0 g $L^{-1}$; the final concentration of pyrene was fixed at $6.0 10^{-7}$ mol $dm^{-3}$. A drop of 2 M NaOH solution was added to each copolymer solution to obtain pH 9; this pH adjustment caused micelles to be formed in situ. Each copolymer solution was left for three days at room temperature to ensure equilibration between the pyrene in the micelles and that in the aqueous solution. Pyrene excitation spectra were recorded at 25° C. on the same fluorescence spectrometer as that described above using an emission wavelength of 373 nm. The emission and excitation slit widths were set at 10 and 2.5 nm, respectively. Spectra were accumulated with a signal-to-noise ratio of 1,000. Pyrene fluorescence is a very sensitive technique for detecting the formation of block copolymer micelles. Pyrene is highly hydrophobic and has very low solubility in water so it migrates preferentially into the hydrophobic micelle cores. Thus a red shift is observed in the pyrene fluorescence spectra and there are also changes in relative peak intensities in the vibrational fine structure. FIG. 19 shows this difference in the spectra for an MPC-DEA diblock copolymer at different pHs (pH4 and 10). Note the intensity of the 13 peak at 373 nm.

Figure 20:
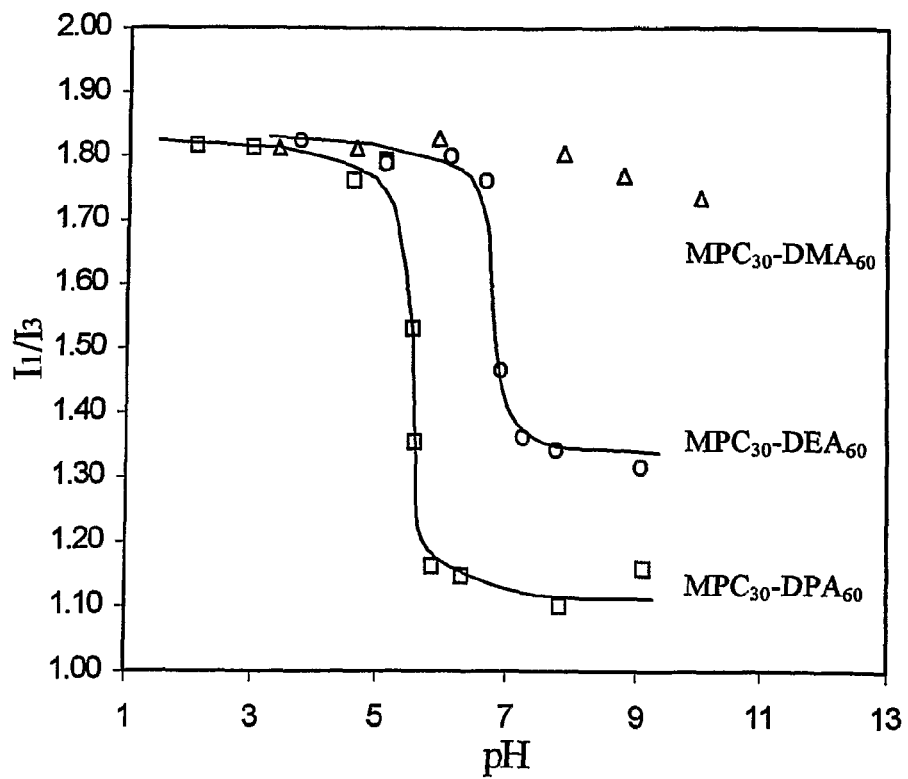

In this example the protocol based on the analysis of pyrene emission spectra reported by Gast and co-workers was employed (Lee, A. S.; Gast, A. P.; Bütüin, V.; Armes, S. P. *Macromolecules* 1999, 32, 4302). The test was carried out at 25° C. from pyrene emission spectra (excitation wavelength $\lambda_{ex}$=333 nm; the diblock copolymer concentration in each case was 0.50 $gl^{-1}$. FIG. 20 shows the variation in the intensity ratio $(I_1/I_3)$ vs. solution pH for three MPC-based diblock copolymers. As the solution pH is increased, the tertiary amine methacrylate residues become progressively deprotonated. The critical pH for micellization was estimated from the reduced $I_1/I_3$ ratio, which indicates a more hydrophobic (micellar) environment for the pyrene probe (in the case of the $MPC_{30}$-$DMA_{60}$ diblock copolymer, there was very little reduction in the $I_1/I_3$ ratio, hence either no micelles are formed under these conditions or the micelles are not hydrophobic enough to ensure efficient pyrene uptake).

The critical micellization pH values estimated for the $MPC_{30}$-$DPA_{60}$ and $MPC_{30}$-$DEA_{60}$ diblock copolymers using this method are pH 5.6 and pH 6.9, respectively. These values correlate quite well with the known pKa's of 6.0 and 7.3 for DPA and DEA homopolymer reported by Bütüin et al (Bütüin, V.; Armes, S. P.; Billingham, N.C. *Polymer,* 2001, 42, 5993).

It is also noteworthy that the plateau value for the $I_1/I_3$ ratio observed at high pH is indicative of the relative hydrophobicity of the micelle cores. The plateau value of approximately 1.15 obtained for the $MPC_{30}$-$DPA_{60}$ diblock copolymer micelles is comparable to that observed by Wilhelm et al. for polystyrene-core micelles and suggests that highly hydrophobic micelle cores are formed (Wilhelm, M.; Zhao, C.-L.; Wang, Y.; Xu, R.; Winnik, M. A.; Mura, J.-L.; Riess, G.; Croucher, M. D. *Macromolecules* 1991, 24, 1033). In contrast, the micelles formed by the $MPC_{30}$-$DEA_{60}$ diblock copolymer clearly have significantly less hydrophobic character.

This hypothesis was supported by further fluorescence studies in order to determine the degree of pyrene partitioning within the micelles. Here the protocol reported by Eisenberg and co-workers was adopted (Astafieva, I.; Zhong, X. F.; Eisenberg, A.; Macromolecules 1993, 26, 7339). Assuming that the DEA and DPA micelle core densities are around 1.0 g cm$^{-3}$, the pyrene partition coefficients for the $MPC_{30}$-$DEA_{60}$ and $MPC_{30}$-$DPA_{60}$ diblock copolymer micelles were calculated to be $3.210^4$ and $1.1 \cdot 10^5$, respectively. Thus the pyrene partition coefficient for the DPA-core micelles is close to the value of $1.9$-$2.4'10^5$ reported for highly hydrophobic polystyrene micelle cores. On the basis of our fluorescence studies, it is anticipated that, compared to the MPC-DEA diblock copolymers, the MPC-DPA diblocks should form more stable micelles with higher loading capacities for the encapsulation of various 'actives' such as hydrophobic drugs.

Example 14

Other Drug Loading Studies

In another example of drug loading, a solution of the drug dipyridamole was used given the intensely coloured nature of the drug allows simple detection. At pH 2 this drug was dissolved to give a fluorescent green-yellow solution. By adjusting the pH to 9-10 the drug was seen to precipitate. Upon adding a solution (at pH 2) of a triblock copolymer of MPC30-DMA30-DEA40 (mixed tunable hydrophobic diblock) to the precipitated drug solution at pH9-10, the drug was rapidly solubilised into the hydrophobic micelle cores that formed to give a classically micellar solution.

EXAMPLE 15

Loading of Micelles by a Solvent Injection Method

MPC100-DPA100 was dissolved in ethanol at a concentration of 40 m/ml. 100 ml of this solution was added dropwise to 9900 µl of phosphate buffered saline (PBS) (1 in 100 dilution), pH 7.3, whilst being stirred with a 1 cm magnetic stirrer at maximum RPM setting. (Actual speed of stirring still to be confirmed using a calibrated strobe light). The stirring was continued for 2 minutes following the polymer/ethanol injection, and the sample then bath sonicated for 5 minutes. The 1 in 100 dilution produced a final MPC100-DPA100 concentration of 0.4 mg/ml (0.008 mM). For drug analogue loading, Orange OT dye was dissolved in the ethanol prior to the MPC100-DPA100, at a polymer/dye mol:mol ratio of 1:0.5. This was then injected (1 in 100) into PBS under the same conditions as for the unloaded MPC100-DPA100, to give MPC100-DPA100 0.4 mg/ml (0.008 mM) with Orange OT at 0.004 mM.

Figure 21:
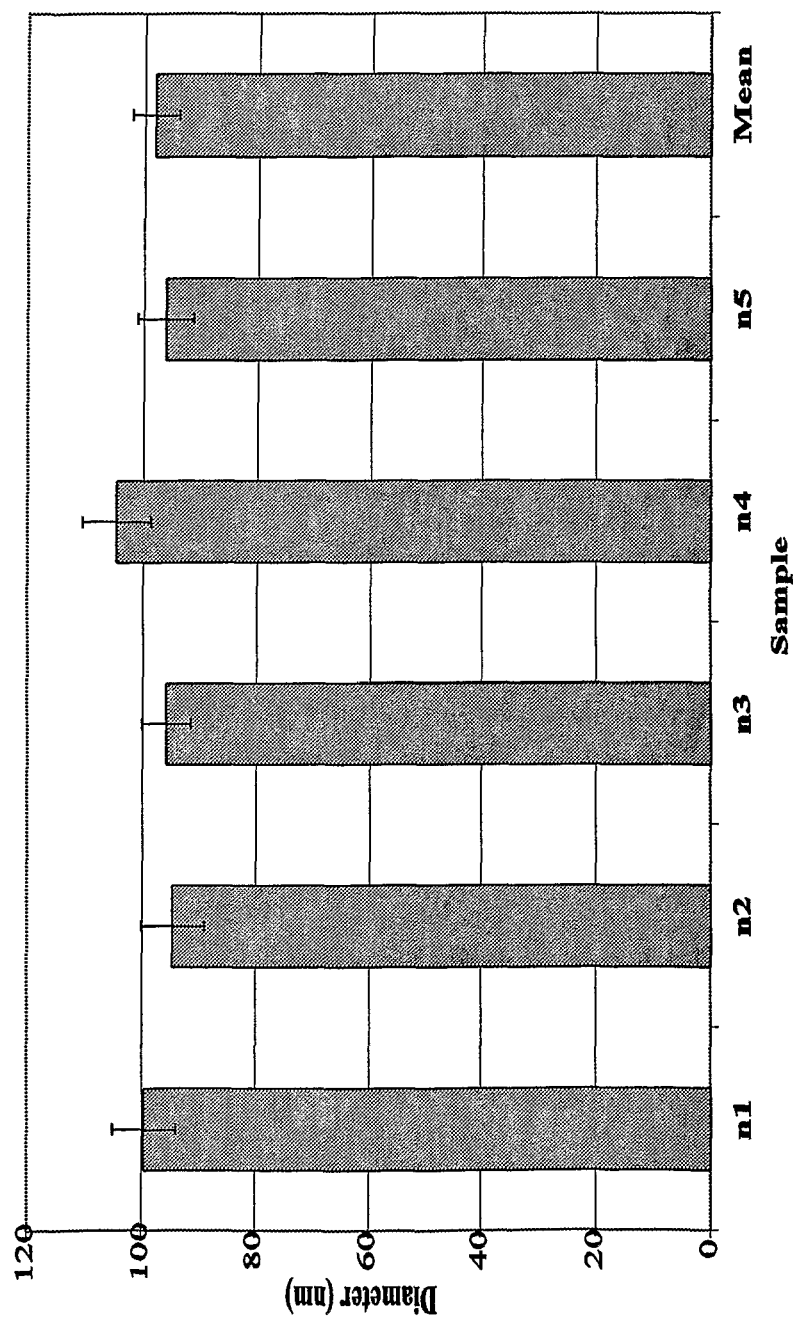
FIGS. 21 to 23 show the results of Example 15.

MPC100-DPA100 solvent injection micelle size, loaded and unloaded, was measured (n=5) in PBS, pH 7.3, at 25° C., using photon correlation spectroscopy (PCS). The effect of polymer concentration on micelle size was examined, by making a series of 50% dilutions with PBS, pH7.3, and measuring particle size using PCS. Temperature effects on the solvent injected MPC100-DPA100, was examined from 5° C. to 70° C., at 5° C. intervals, using PCS to measure particle size. In FIG. 21 for samples n1 to n5$^-$ the error bars represent the standard deviations for 6 measurements for each sample. Sample "mean" is the mean of samples n1 to n5 and the error bar represents the standard deviation between the 5 samples.

Figure 22:
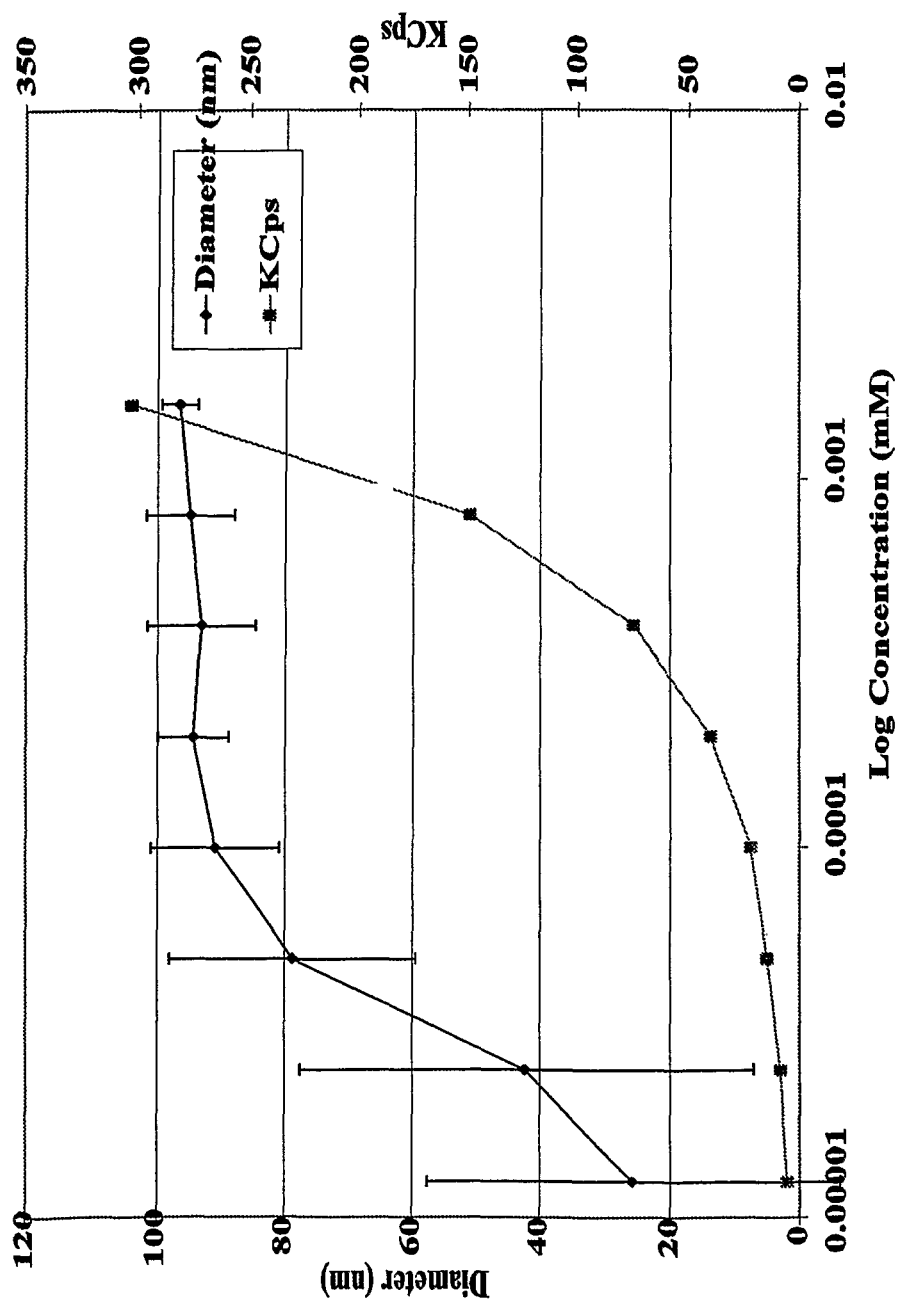

There is no apparent difference in mean diameter between the loaded and unloaded solvent injection micelles, both approximately 98 nm (n=5, +/−SD). Both the loaded and unloaded solvent injection MPC100-DPA100 micelles are stable/detectable down to 0.0001 mM concentration (0.005 mg/ml), which is 10 times lower than the lowest detectable concentration for MPC100-DPA100 micelles produced previously by the pH increase method (FIGS. 21 & 22). FIG. 22 represents the results of sample n=1 and the error bars represents the standard deviation of 6 measurements for each concentration point.

Figure 23:
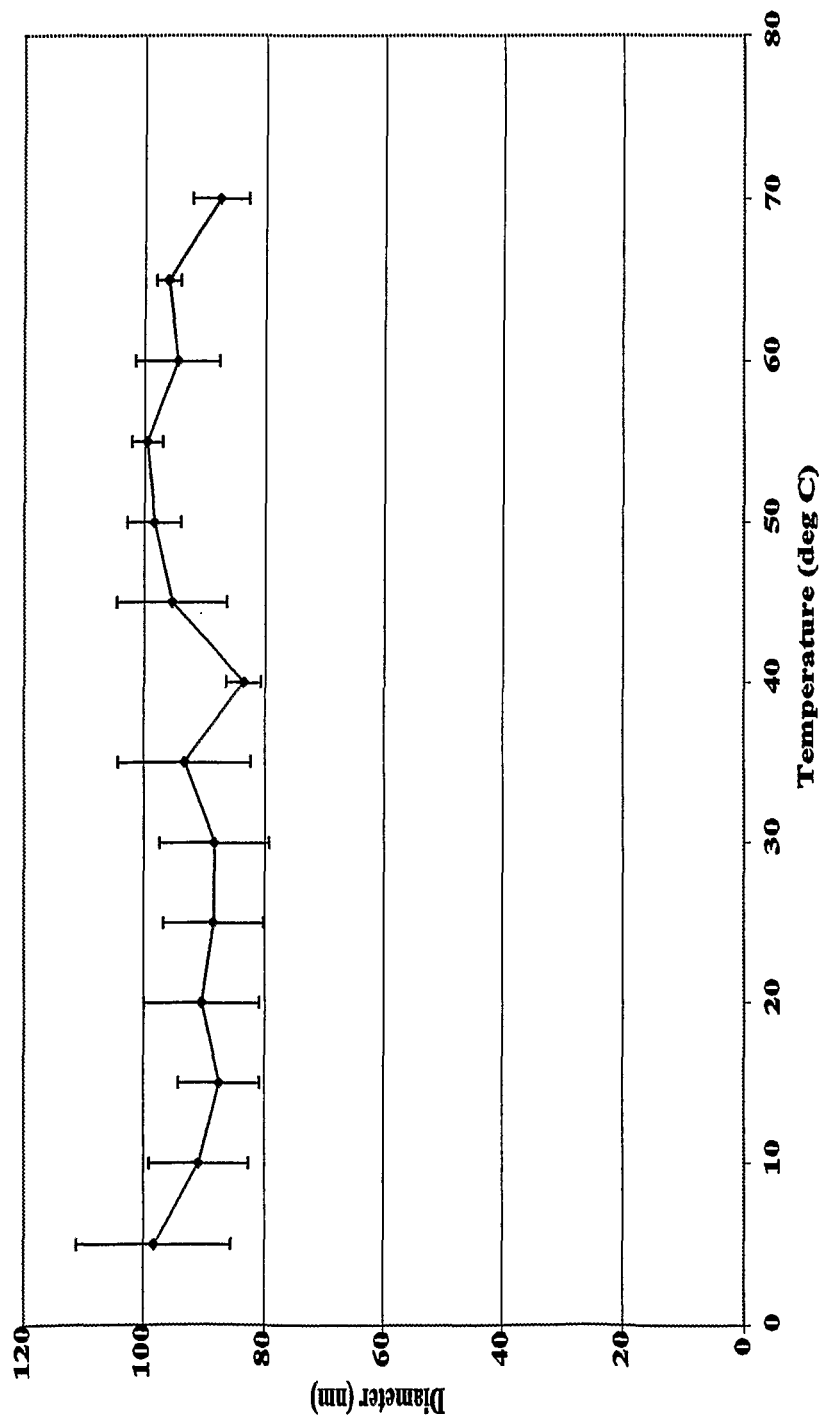

The solvent injection MPC100-DPA100 micelles, both loaded and unloaded, appear stable from 5° C. to 70° C. At 40° C. for both the loaded and unloaded MPC100-DPA100 micelles, the systems appeared to tighten, with a reduction in mean particle diameter and SD between the 6 measurements at that temperature (FIG. 23 shows sample n=1 and the error bars represent the standard deviation of 6 measurements for each concentration point).

EXAMPLE 16

Assessment of Cell Toxicity Methodology

To determine cell toxicity and also potential toxicity reducing properties of the diblock polymers, a cell formation cytotoxicity assay is used as described below:

The polymers to be tested are prepared in phosphate buffered saline by solvent injection. V79 hamster lung macrophages in DMEM media supplemented with 10% foetal calf serum (FCS) and 1% penstrep (P/S) are seeded at 100 cells in 500 µl per well of a 24 well plate (Iwaki). These are incubated at 37° C., in 5% $CO_2$, for 24 hours. The polymer samples are sterile filtered using 0.45 µm syringe filters (Nalge Nunc). Dilutions of the polymer solutions are prepared in DMEM supplemented with 2.5% FCS and 1% P/S. After the 24 hours incubation the media is removed from the cells in the wells and 500 µl of each dilution added to individual wells, where n=8 for each dilution. A control plate of the DMEM supplemented with 2.5% FCS and 1% P/S is run alongside to provide a 100% survival figure. These are all then incubated at 37° C., in 5% $CO_2$, for 5 days. After the 5 days the media is removed and the cells fixed with gluteraldehyde (in house) for 30 minutes. This is then removed, the cells washed with deionised water, and stained with 10% giemsa stain in water, for 30 minutes. The stain is then removed and the cell colonies present in each well counted. By comparing the number of colonies from the test samples against the control sample, a survival figure can be produced for each polymer concentration and the concentration which reduces colony numbers by 50% (EC$_{50}$) determined.

A kill curve for doxorubicin can be constructed by substituting dilutions of doxorubicin in ethanol for the polymers in the assay above. This enables determination of the EC50 for doxorubicin.

Polymer micelles loaded with doxorubicin can be prepared by solvent injection. The doxorubicin is dissolved in ethanol, and the polymer then dissolved in the ethanol/doxorubicin. Injection of a small volume of the polymer/doxorubicin/ethanol into a larger volume of PBS, for example 1 in 100 dilution, whilst the PBS is stirred results in the formation of doxorubicin loaded polymer micelles. If the loaded micelles are substituted for the polymers in the assay above then the EC50 can be determined. By varying the ratio of doxorubicin to polymer and comparing the result against the doxorubicin kill curve, it is possible to determine whether the loaded micelles reduce the toxicity of the doxorubicin, and also the maximum loading capability of the polymer/micelles.

EXAMPLE 17

Pharmacokinetics of MPC-Micelle and Doxorubicin in Experimental Colon Tumour Models There are already several established protocols that describe methods for assessing block copolymer-based formulations from cell-screening through to clinical studies (see Alakhov, V. et al., Block copolymer-based formulations of doxorubicin. From cell screen to clinical trials, Colloids & Surfaces, B: Biointerfaces (1999), 16(1-4), 113-134).

The activity of doxorubicin PC-micelles will be determined using two tumour models. The MAC15A tumour and MAC26 tumour have been widely used in the evaluation of anticancer agents. MAC15A is a poorly differentiated, rapidly growing adenocarcinoma that becomes necrotic, and cells are associated with blood vessels in typical tumour cords. MAC26 is a well differentiated glandular adenocarcinomal with a clear stromal component and well-developed blood supply.

Tumours: Groups of 5 to 10 tumour-bearing mice will be treated with either free doxorubicin at previously established maximum tolerated dose (10 mg/kg, single iv) or doxorubicin-loaded MPC micelles at equivalent dose. Treatment will commence when tumours can be reliably measured by callipers (mean dimensions, 7×10 cm). Therapeutic effect will be measured by twice weekly calliper measurement of the tumour.

Pharmacokinetics: At various time points after administration of free doxorubicin or doxorubicin-loaded MPC micelles, mice will be anaesthetised and blood samples taken via cardiac puncture. Blood samples will be kept at 4° C. until centrifugation (1000×g for 5 mins at 4° C.). Samples of tumours will be taken and placed into liquid nitrogen. Pharmacokinetic parameters will be estimated by standard non-compartmental methods. Terminal elimination rate will be calculated using linear regression analysis of the terminal log linear portion of the curve.

Doxorubicin Extraction: Doxorubicin will be extracted from plasma and tumours based on a method developed by Fraier et al. HPLC with fluorimetric detection. (J. Pharm. Biomed. Anal., 13: 625-633 1995). Samples will then analysed by standard HPLC methods using fluorescence detection. This method is capable of separating several doxorubicin metabolites.

What is claimed is:

1. An aqueous composition comprising an amphiphilic block copolymer having a hydrophilic block and a hydrophobic block, dispersed in a solution, and a biologically active compound associated with the copolymer, wherein the hydrophilic block has pendant zwitterionic groups, a log concentration (μg/ml) of the amphiphilic block copolymer in the aqueous composition is from 0.1 to 100, the copolymer comprising a hydrophilic block formed by radical polymerisation of an ethylenically unsaturated zwitterionic monomer, which is 2-methacryloyloxyethyl-2'-trimethylammonium ethyl phosphate inner salt, and a hydrophobic block formed from (diisopropyl-amino)ethyl methacrylate, the aqueous composition comprising micelles of the copolymer and the biologically active compound associated with the copolymer in the micelles, the pH of the aqueous composition being 6.5 to 7.4 whereby the copolymer is above the critical micelle concentration in the aqueous composition.

2. A composition according to claim 1 in which the biologically active molecule is associated by hydrophobic interactions with the copolymer.

3. A composition according to claim 2 in which the biologically active compound has a measured and/or calculated partition coefficient between octanol and water of at least 1.0.

4. A composition according to claim 1 in which the hydrophobic block comprises pendant groups which are ionisable, having a pK$_A$ or pK$_B$ in the range 4 to 10.

5. A composition according to claim 1 in which the hydrophillic block is formed by radical polymerization of the 2-methacryloyloxyethyl-2'-trimethylammonium ethyl phosphate inner salt and comonomer.

6. A composition according to claim 5 in which the comonomer has the general formula VIII

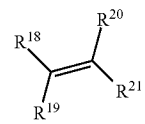

VIII in which R$^{18}$ is selected from the group consisting of hydrogen, halogen, C$_{1-4}$ alky and groups COOR$^{22}$ in which R$^{22}$ is hydrogen and C$_{1-4}$ alkyl;
R$^{19}$ is selected from the group consisting of hydrogen, halogen and C$_{1-4}$ alkyl;
R$^{20}$ is selected from the group consisting of hydrogen, halogen, C$_{1-4}$ alkyl and groups COOR$^{22}$ provided that R$^{18}$ and R$^{20}$ are not both COOR$^{22}$; and
R$^{21}$ is selected from the group consisting of C$_{1-10}$ alkyl, C$_{1-20}$ alkoxycarbonyl, mono- or di-(C$_{1-20}$ alkyl) amino carbonyl, C$_{6-20}$ aryl (including alkaryl) C$_{7-20}$ aralkyl, C$_{6-20}$ aryloxycarbonyl, C$_{1-20}$ -aralkyloxycarbonyl, C$_{6-20}$ arylamino carbonyl, C$_{7-20}$ aralkyl-amino, hydroxyl and C$_{2-10}$ acyloxy groups, any of which may have one or more substituents selected from the group consisting of halogen atoms, and alkoxy, oligo-alkoxy, aryloxy, acyloxy, acylamino, amine, carboxyl, sulphonyl, phosphoryl, phosphino, zwitterionic, hydroxyl, vinyloxycarbonyl, and reactive silyl and silyloxy groups;
or R$^{21}$ and R$^{20}$ or R$^{21}$ and R$^{19}$ may together form —CONR$^{23}$CO in which R$^{23}$ is a C$_{1-20}$ alkyl group.

7. A composition according to claim 6 in which the comonomer is selected from the group consisting of C$_{1-24}$ alkyl(alk)-acrylates, $C_{1-24}$-alkyl(alk)-acrylamides, mono- and di-hydroxy-$C_{1-6}$-alkyl(alk)-acrylates, mono- and di-hydroxy-$C_{1-6}$-alkyl(alk)acrylamides, oligo($C_{2-3}$ alkoxy) $C_{2-18}$ alkyl(alk)-acrylates, $C_{2-18}$ alkyl(alk)acrylamides, styrene, vinylacetate and N-vinyllactam.

8. A composition according to claim 1 in which the polydispersity of molecular weight of each of the blocks is less than 2.0.

9. A composition according to claim 1 in which the degree of polymerisation of the hydrophilic block is in the range 2 to 1000.

10. A composition according to claim 1 in which the degree of polymerisation of the hydrophobic block is in the range 5 to 2000.

11. A composition according to claim 9 in which the ratio of the degrees of polymerisation of the hydrophobic to hydrophilic blocks is in the range 1:5 to 10:1.

12. A composition according to claim 1 in which the radical polymerisation is a controlled radical polymerisation.

13. A composition according to claim 12 in which the polymerisation is an atom transfer radical polymerisation or group transfer polymerisation.

14. A composition according to claim 13 in which the initiator for the radical transfer polymerisation process is a polymer compound in which the polymeric moiety is hydrophobic which forms the hydrophobic block of the copolymer.

15. A composition according to claim 13 in which the hydrophobic block is also formed from ethylenically unsaturated monomers by a radical transfer polymerisation process.

16. A composition according to claim 1 in which the biologically active molecule is a cytotoxic compound.

17. A method of forming an aqueous composition comprising an amphiphilic block copolymer and a biologically active compound, in which the copolymer comprises a hydrophilic block formed by radical polymerisation of an ethylenically unsaturated zwitterionic monomer, which is 2-methacryloyloxyethyl-2'-trimethylammonium ethyl phosphate inner salt and a hydrophobic block formed from (diisopropyl-amino)ethyl methacrylate in which process an aqueous dispersion of empty copolymer micelles is formed and the micellar dispersion is contacted with biologically active compound under conditions such that the biologically active compound becomes associated with the copolymer in the micelles, wherein the hydrophilic block has pendant zwitterionic groups, in which the biologically active compound has a partition coefficient between octanol and water of at least 1.0, and in which the hydrophobic block of the copolymer comprises ionisable groups which are primary, secondary or tertiary amine groups, and in which the empty copolymer micelles are formed by a process comprising:
   a) a first copolymer dissolution step in which the block copolymer, with the groups of hydrophobic block in at least partially ionised form, is dissolved in an aqueous liquid, and
   b) a second micelle forming step in which the conditions in the solution are adjusted by raising the pH to a pH of 6.5 to 7.4 so that the ionised groups are converted at least partially to their deprotonated form, whereby the copolymer is above the critical micelle concentration in the aqueous liquid and micelles are formed, wherein a log concentration (µg/ml) of the amphiphilic block copolymer in the aqueous composition is from 0.1 to 100.

18. A method according to claim 17 in which the conditions which are adjusted are of temperature and pH.

19. A method according to claim 17 in which the biologically active compound is in solid form when it is contacted with the aqueous dispersion of empty micelles.

20. A method according to claim 17 in which the biologically active compound is in solution in an organic solvent when it is contacted with the aqueous dispersion of empty micelles.

21. A composition according to claim 3 in which the partition coefficient is at least 1.5.

22. A composition according to claim 1 in which the hydrophillic block is formed from (diisopropyl-amino)ethyl methacrylate and comonomer.

23. A composition according to claim 22 in which the comonomer has the general formula VIII

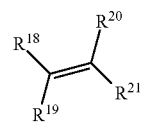

VIII in which $R^{18}$ is selected from the group consisting of hydrogen, halogen, $C_{1-4}$ alkyl and groups $COOR^{22}$ in which $R^{22}$ is hydrogen or $C_{1-4}$ alkyl;

$R^{19}$ is selected from the group consisting hydrogen, halogen and $C_{1-4}$ alkyl;

$R^{20}$ is selected from the group consisting of hydrogen, halogen, $C_{1-4}$ alkyl and groups $COOR^{22}$ provided that $R^{18}$ and $R^{20}$ are not both $COOR^{22}$;

$R^{21}$ is selected from the group consisting of $C_{1-10}$ alkyl, $C_{1-20}$ alkoxycarbonyl, mono- or di-($C_{1-20}$ alkyl) amino carbonyl, $C_{6-20}$ aryl, $C_{7-20}$ aralkyl, $C_{6-20}$ aryloxycarbonyl, $C_{1-20}$-aralkyloxycarbonyl, $C_{6-20}$ arylamino carbonyl, $C_{7-20}$ aralkyl-amino, hydroxyl and $C_{2-10}$ acyloxy group, any of which may have one or more substituents selected from the group consisting of halogen atoms and alkoxy, oligo-alkoxy, aryloxy, acyloxy, acylamino, amine, carboxyl, sulphonyl, phosphoryl, phosphino, zwitterionic, hydroxyl, vinyloxycarbonyl, and reactive silyl and silyloxy groups, or $R^{21}$ and $R^{20}$ or $R^{21}$ and $R^{19}$ may together form —$CONR^{23}CO$ in which $R^{23}$ is a $C_{1-20}$ alkyl group.

24. A composition according to claim 23 in which the comonomer is selected from the group consisting of $C_{1-24}$ alkyl(alk)acrylates, $C_{1-24}$ alkyl(alk)acrylamides, mono- and di-hydroxy-$C_{1-6}$ alkyl(alk)acrylates, mono- and di-hydroxy-$C_{1-6}$-alkyl(alk)acrylamides, oligo($C_{2-3}$ alkoxy) $C_{2-18}$-alkyl (alk)acrylates, $C_{2-18}$ alkyl(alk)acrylamides, styrene, vinylacetate and N-vinyllactam acrylamides, mono- and di-hydroxy-$C_{1-6}$-alkyl(alk)acrylates, and acrylamides, oligo ($C_{2-3}$ alkoxy) $C_{2-18}$-alkyl(alk)acrylates, and acrylamides, styrene, vinylacetate and N-vinyllactam.

25. A composition according to claim 8 in which the polydispersity is in the range 1.1 to 1.4.

26. A composition according to claim 9 in which the degree of polymerisation is in the range 10 to 100.

27. A composition according to claim 10 in which the degree of polymerisation is in the range 20 to 250.

28. A method according to claim 17 in which the biologically active molecule is a cytotoxic compound.

29. A method according to claim 17 in which the radical polymerisation is a controlled radical polymerisation.

30. A composition according to claim 10 in which the ratio of the degrees of polymerisation of the hydrophobic to hydrophilic blocks is in the range 1:5 to 10:1.

* * * * *